US011921074B2

United States Patent
Meyer et al.

(10) Patent No.: US 11,921,074 B2
(45) Date of Patent: Mar. 5, 2024

(54) GAS-SENSITIVE DEVICE

(71) Applicant: Infineon Technologies AG, Neubiberg (DE)

(72) Inventors: Markus Meyer, Sinzing (DE); Werner Breuer, Sinzing-Viehhausen (DE)

(73) Assignee: Infineon Technologies AG, Neubiberg (DE)

( * ) Notice: Subject to any disclaimer, the term of this patent is extended or adjusted under 35 U.S.C. 154(b) by 162 days.

(21) Appl. No.: 17/453,410

(22) Filed: Nov. 3, 2021

(65) Prior Publication Data
US 2022/0163475 A1    May 26, 2022

(30) Foreign Application Priority Data

Nov. 20, 2020    (EP) .................................. 20208978

(51) Int. Cl.
*G01N 27/22*      (2006.01)
*G01N 33/00*      (2006.01)

(52) U.S. Cl.
CPC ....... *G01N 27/221* (2013.01); *G01N 33/0009* (2013.01); *G01N 2027/222* (2013.01)

(58) Field of Classification Search
CPC .................. G01N 27/221; G01N 2027/222
See application file for complete search history.

(56) References Cited

U.S. PATENT DOCUMENTS

| 4,953,387 | A | * | 9/1990 | Johnson | G01N 27/12 73/25.03 |
|---|---|---|---|---|---|
| 8,739,622 | B2 | * | 6/2014 | Grange | H01G 5/0134 73/335.04 |
| 2011/0045601 | A1 | * | 2/2011 | Gryska | G01N 27/221 422/82.01 |
| 2014/0077314 | A1 | * | 3/2014 | Humbert | G01N 27/227 438/49 |
| 2014/0260545 | A1 | * | 9/2014 | Ruhl | G01N 27/124 73/31.05 |
| 2015/0153297 | A1 | | 6/2015 | Aliane et al. | |
| 2019/0293596 | A1 | | 9/2019 | Nakamura et al. | |

FOREIGN PATENT DOCUMENTS

| DE | 102011002854 A1 | 2/2012 |
|---|---|---|
| EP | 3598118 A1 | 1/2020 |

\* cited by examiner

*Primary Examiner* — Kristina M Deherrera
*Assistant Examiner* — Jean F Morello
(74) *Attorney, Agent, or Firm* — Slater Matsil, LLP

(57) ABSTRACT

In accordance with an embodiment, a gas-sensitive device includes a substrate structure, and a gas sensitive capacitor. The gas sensitive capacitor a first capacitor electrode in form of a gas-sensitive layer on a first main surface region of an insulation layer, and a second capacitor electrode in form of a buried conductive region below the insulation layer, so that the insulation layer is arranged between the first and second capacitor electrode. The gas-sensitive layer comprises a sheet impedance which changes in response to the adsorption or desorption of gas molecules.

22 Claims, 20 Drawing Sheets

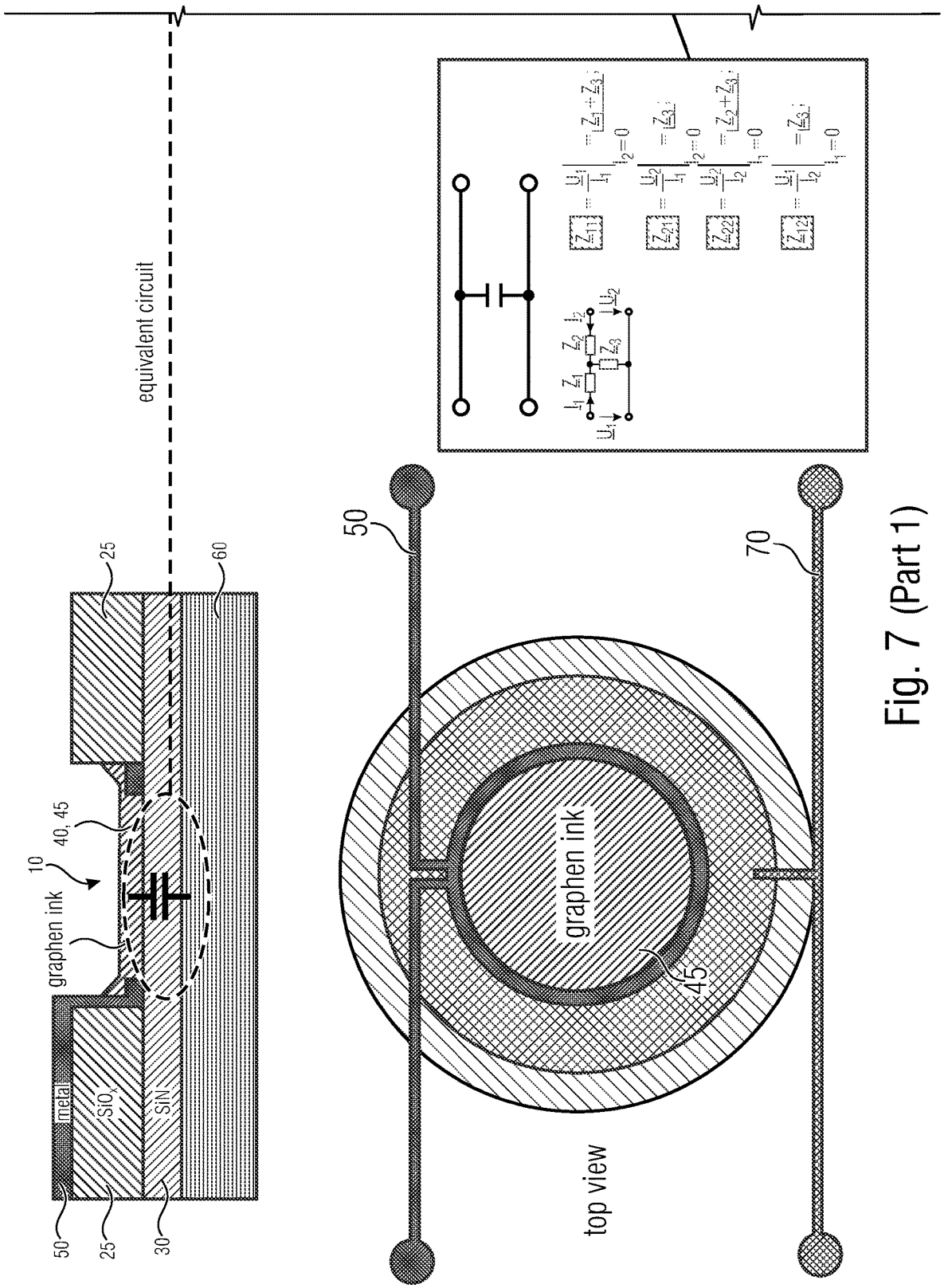
Fig. 7 (Part 1)

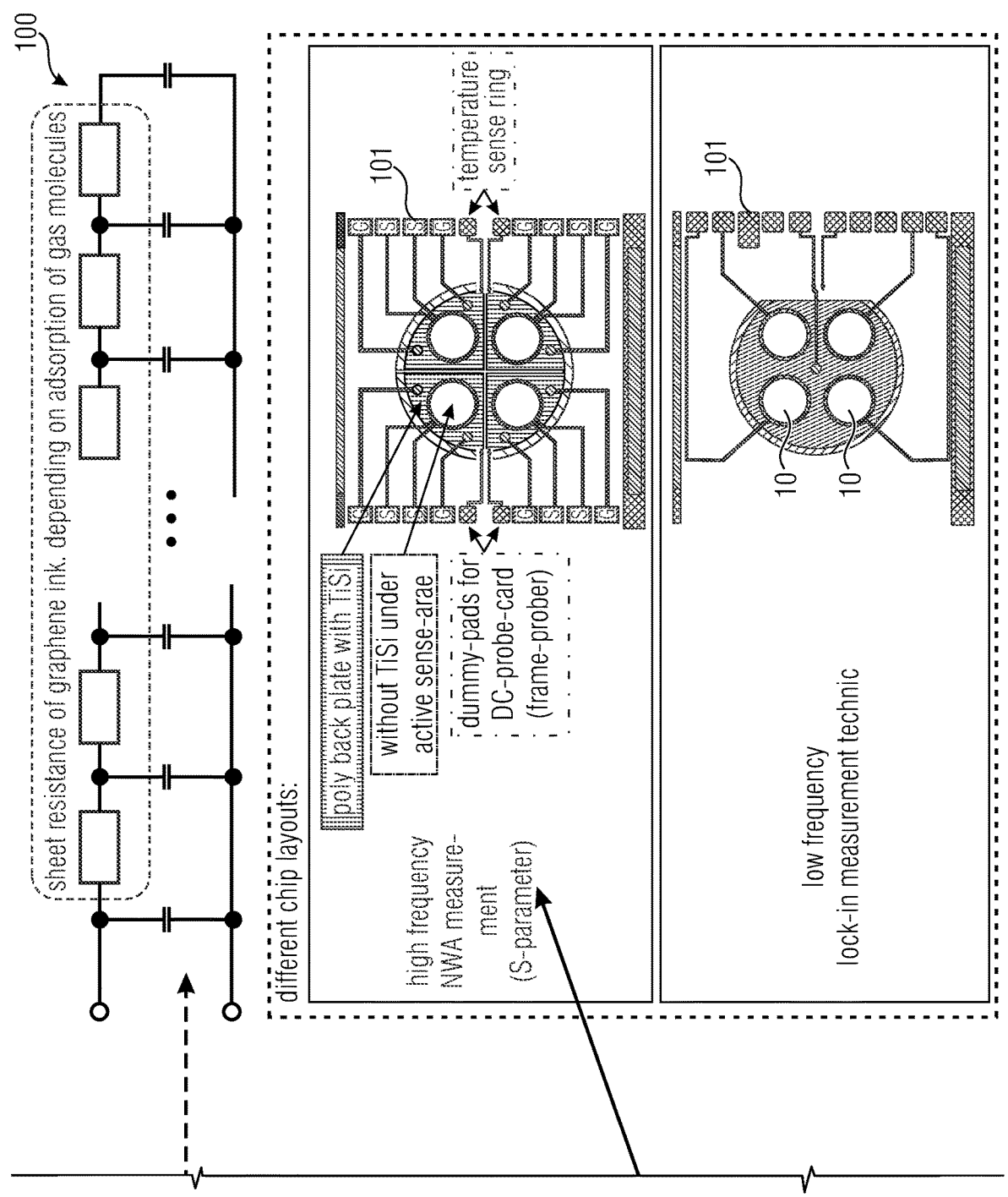
Fig. 7 (Part 2)

Werner Breuer, InnoLab 2020_03-11 low frequency lock-in measurement
→ detection of impedance change at „lower" frequencies Werner Breuer, InnoLab 2020_03-11    R dev. (%)

high frequency NWA measurement
(S-Parameter)
→ detection of capacity changes
at „higher" frequencies

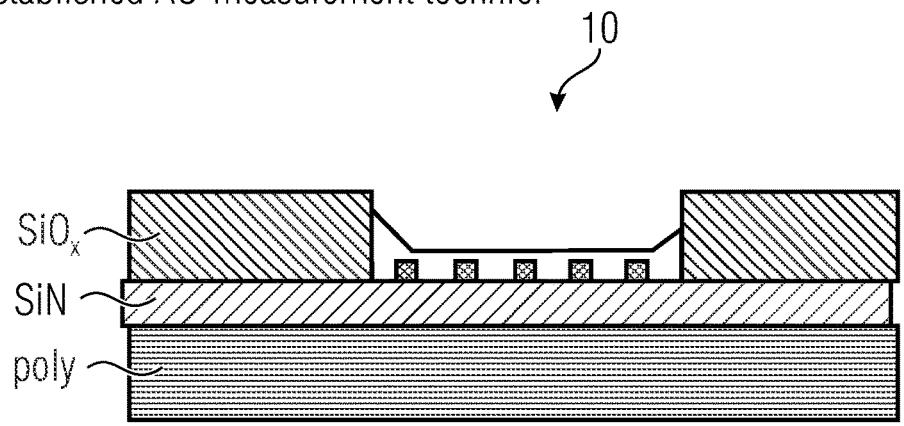
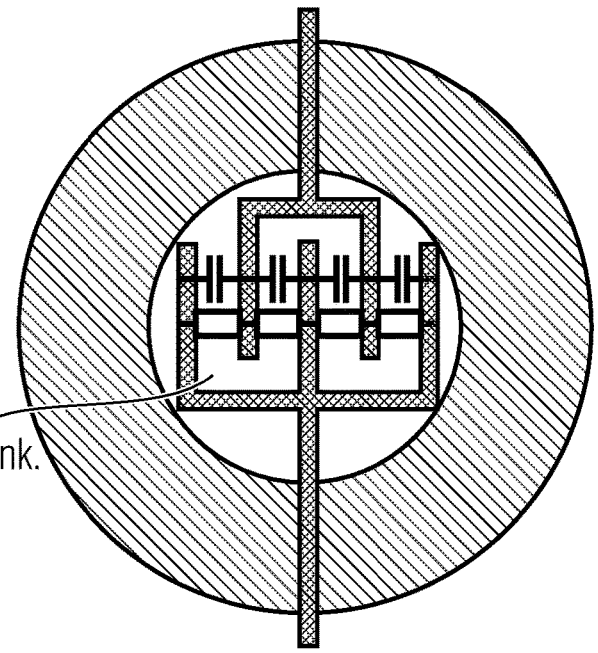
Fig. 9b

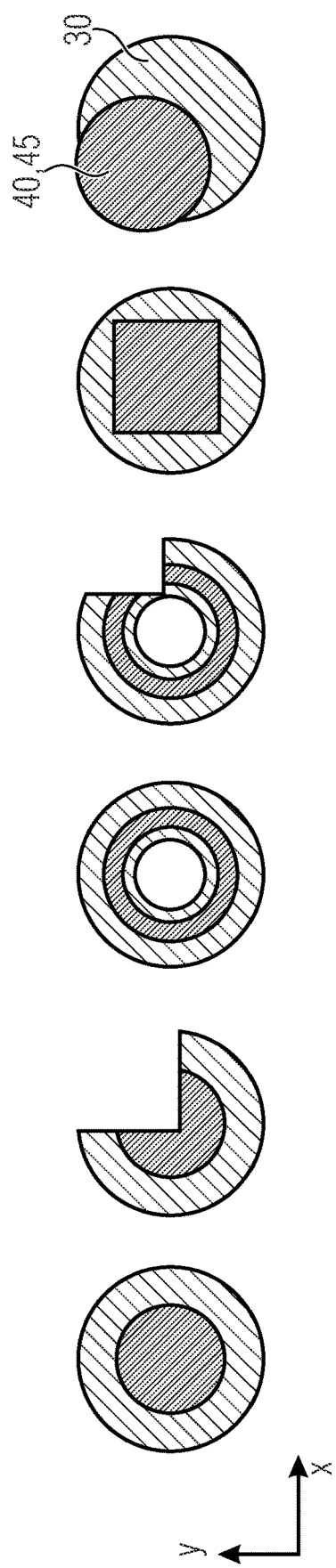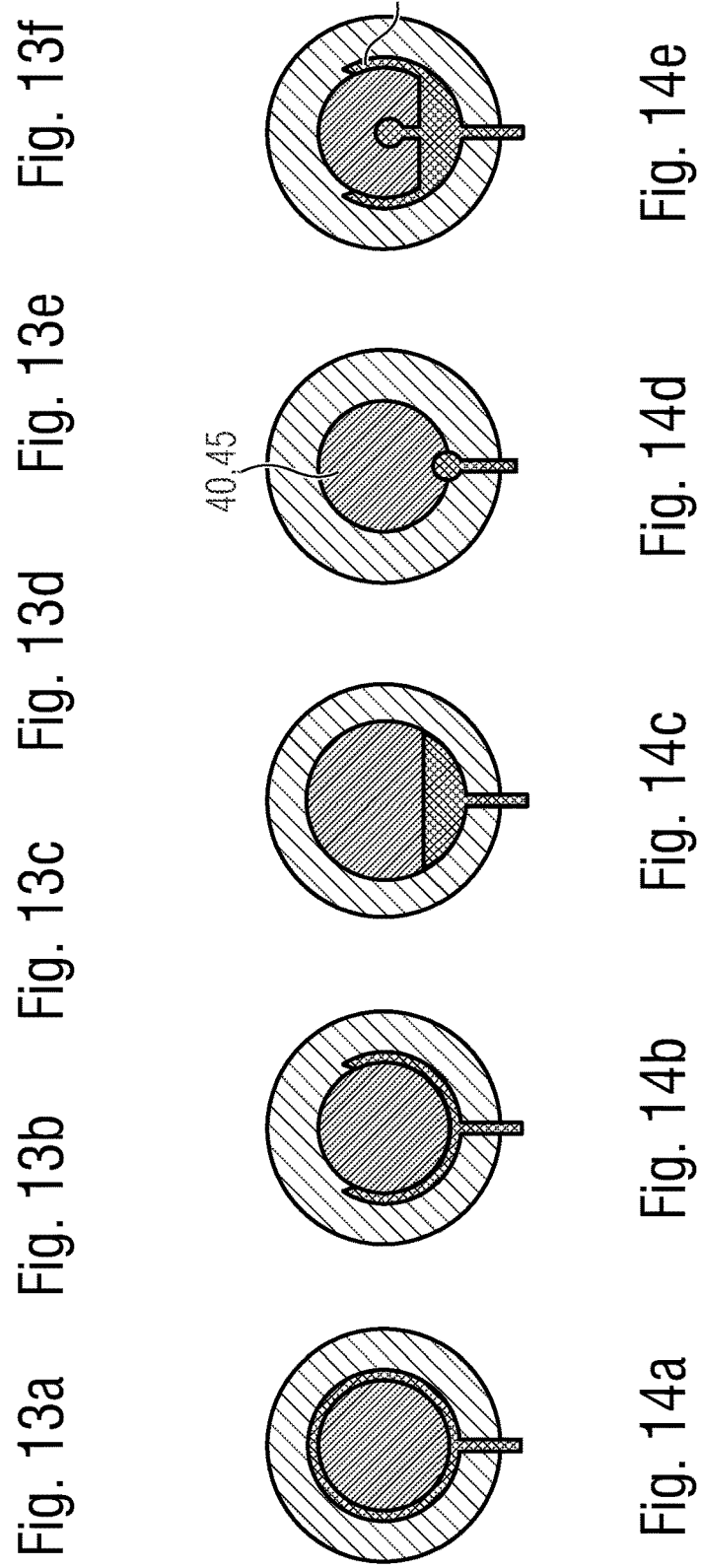

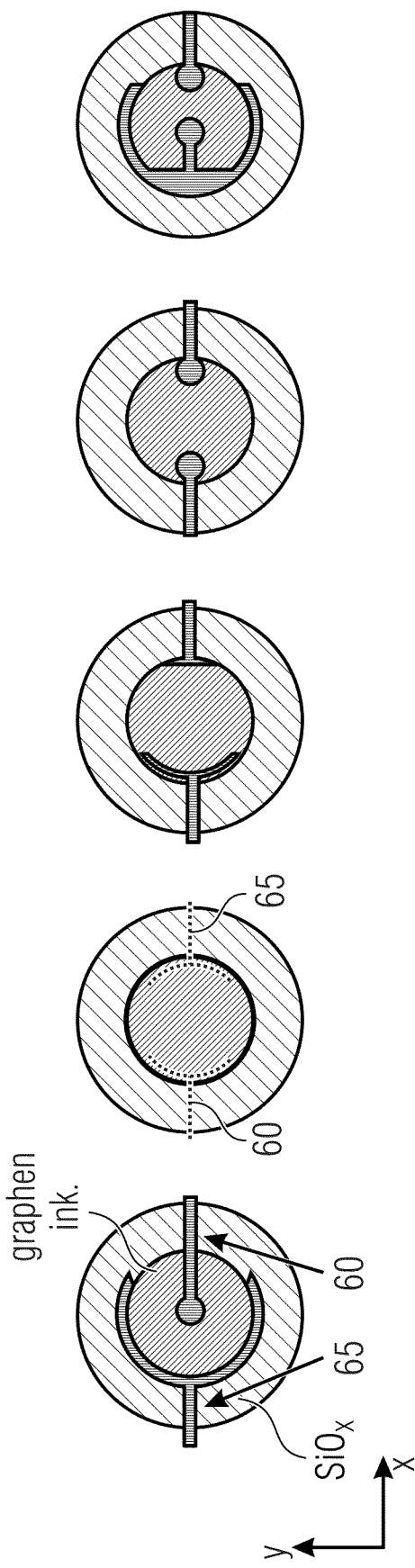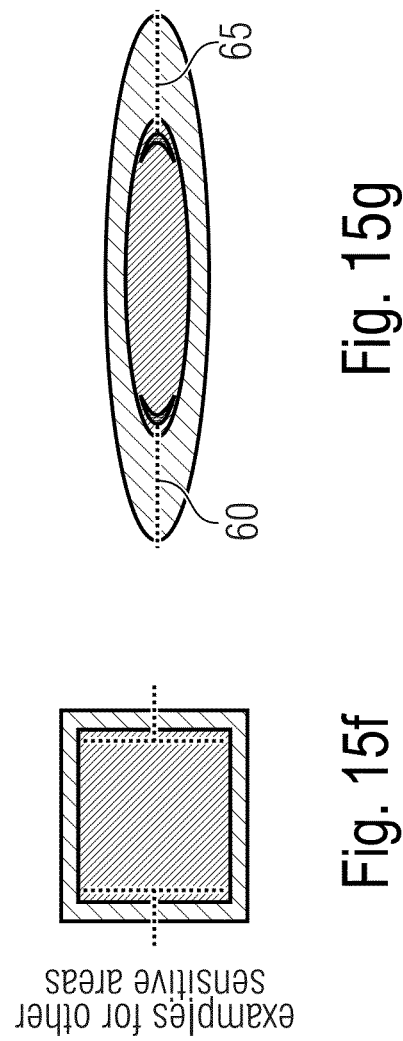

GAS-SENSITIVE DEVICE

This application claims the benefit of European Patent Application No. 20208978, filed on Nov. 20, 2020, which application is hereby incorporated herein by reference.

TECHNICAL FIELD

The disclosure relates in general to a gas sensitive device and a method for operating the gas sensitive device.

BACKGROUND

The detection of environmental parameters, e.g. gas concentrations, in the ambient atmosphere is becoming increasingly important in the implementation of appropriate sensors within mobile devices, but also in the application in home automation, such as smart home and, for example, in the automotive sector. However, with the evermore extensive use of gas sensors, there is also a particular need to be able to monitor the quality of the ambient atmosphere, i.e. to determine the air quality using mobile devices. Such an air quality monitoring process should be inexpensively and cost-effectively implemented. To be more specific, for a best efficiency the entire gas sensor should act as an active gas sensing area. The more area the gas sensitive device provides, the higher is its sensitivity and therewith its efficiency. Usually, a graphene area is used to monitor the ambient air quality.

An ongoing trend in the evolution of mobile devices (smart phones, etc.) is the implementation of more and more additional features. One of the highly expected next steps will be the integration of gas sensors measuring air quality and/or detecting and warning of toxic air pollution. Therefor "simple" low cost sensor-devices with a small footprint and a very low power consumption are needed.

The deposition of an active sensor layer is a printing process of a solvent consisting of ink, graphene flakes and e.g., nanoparticles for functionalization. During drying, the fluid ink droplets form a so-called coffee-ring at the edge of the sensor area. The result is a thicker sensor layer at the sensor edge. During resistance measurement the current is located at the sensor edge and not homogeneously distributed over the whole sensor area. Thus, only the small current path of the "Coffee-Ring" is contributing to the sensitivity and not the whole sensor area.

Thus, two effects reduce the use of the whole gas sensor area. Firstly, locally clustered graphene flakes between electrodes lead to a reduction of the area usable for resistance measurements. Because of the clustered graphene flakes between electrodes printed on top of a substrate area a conductance only between a few electrodes usually result. Secondly, during the manufacturing process of producing the electrodes on the top surface of the substrate coffee stain arises. Coffee stain causes a surrounding shortage between the incoming metal lines, so that the conductance is only given at outer sensor edges. Both effects suppress the use of the whole sensing area and reduce the efficiency of the sensor.

An established concept is a printed or dispensed active sensor-layer consisting of graphene flakes and functional nanoparticles on top of an interdigital structure (as shown in FIG. 9b). The adsorption or desorption of gas molecules are reflected by the change of the electrical resistance of the device.

In addition to the mostly dominating coffee-ring-effect, the metal lines of the interdigital structure can cause accumulation and clumping of ink ingredients between two metal fingers. In this case, also only a small area is defining the sensitivity and not the whole sensor area.

Thus, a conventional method of gas measurement is measuring the resistance-change of a gas sensitive layer between the electrodes of an interdigital structure. This method has two disadvantages.

There is an intrinsic problem of the interdigital structure in principle. The interdigital structure forms a parallel circuit over the entire active area. This means, if there is any grain or lump with a higher conductance between two metal fingers, this will determine the resistance of the whole sensor area.

Another Problem is the Coffee-Ring-Effect, typically for the printing process of the sensitive layer. This leads to a conductive path around the sensor area.

Both effects avoid the use of the whole sensor area because any grain or lump with a higher conductance between two metal fingers or higher deposition on a sensor edge will determine the resistance of the whole sensor area.

Generally, there is a need in the art for an approach to implement an improved gas sensitive device and an improved multi-gas sensor and a method of operating the gas sensitive device, that are independent from locally clustered graphene flakes and/or from coffee stain.

SUMMARY

In an embodiment, a gas sensitive device comprises a substrate structure, and a gas sensitive capacitor. The gas sensitive capacitor comprises a first capacitor electrode in form of a gas-sensitive layer on a first main surface region of an insulation layer, and a second capacitor electrode in form of a buried conductive region below the insulation layer. The insulation layer is arranged between the first and second capacitor electrode; wherein the gas-sensitive layer comprises a sheet impedance which changes in response to the adsorption or desorption of gas molecules. The first capacitor electrode is preferably provided on top of the gas sensitive device. Therefore, the first capacitor electrode may be called top electrode. The second capacitor electrode is preferably buried and is provided in the gas sensitive device, in particular above a substrate structure carrying the gas sensitive device. Therefore, the second capacitor electrode may be called buried electrode.

As proposed a gas sensitive layer on top of a flat surface forms the first capacity electrode, i.e. the top electrode, of a gas sensitive capacitor. The second capacity electrode of the capacitor is a buried electrode under a, preferably thin, insulation layer. The top electrode is contacted at the edge. Therefore, the inner part of the top electrode is contacted via the rather high ohmic gas sensitive layer. If gas molecules are adsorbed at the surface by the top electrode, the sheet resistance or sheet impedance will change. This can be measured with the methods described below.

According to an example, a multi-gas sensor comprises one or more gas sensitive devices according to any of the gas sensitive devices disclosed herein. With the disclosed multi-gas sensor it may be possible to distinguish two or more gases with a sensor response of one gas sensitive device as proposed herein.

According to an example, a method for operating the gas sensitive device according to any of the gas sensitive devices disclosed herein is proposed. The method comprises applying an AC signal to the first capacitor electrode; reading out a signal between the first capacitor electrode and the second capacitor electrode, wherein the signal read out comprises information on the sheet resistance or the sheet impedance of the gas-sensitive layer of the first capacitor electrode due to the adsorbed or desorbed gas molecules. The relation between the sheet resistance or the sheet impedance of the sensitive layer and the capacitive impedance causes a frequency dependency of capacity measurement. At low frequencies the capacitance of the whole area can be measured. At high frequencies only the capacitance of the sensor edge can be measured.

In contrast to the usual interdigital structure the proposed gas sensing capacitor is an averaging device. This means local non-homogeneities of the sensing layer are negligible. Also, the coffee ring effect has no negative effect to the gas detection.

The proposed multi-gas sensor and the disclosed method can be implemented with any of the proposed gas-sensitive device described within this application.

BRIEF DESCRIPTION OF THE DRAWINGS

Embodiments of the present methods for providing calibration for a gas sensor device and for calibrating/testing a gas sensor device and embodiments of the gas sensor arrangement for providing calibration data and/or for calibrating the gas sensor device are described herein making reference to the appended drawings and figures.

FIG. 7 shows a schematic view of a gas sensitive device and of an equivalent circuit of an AC-coupled multi gas sensor comprising four gas sensitive devices according to an embodiment;

FIGS. 9a and 9b show a comparison between the proposed gas sensitive device having an AC-coupled sensitive layer versus an established impedance measurement technique;

FIGS. 13a-13f show possible design variants for the gas sensitive area of the gas-sensitive device;

FIGS. 14a-14e show design variants of the contact regions of the gas sensitive device;

FIGS. 15a-15g show variations of the implementation of the gas sensitive device as shown in FIG. 6;

Before discussing the present embodiments in further detail using the drawings, it is pointed out that in the figures and the specification identical elements and elements having the same functionality and/or the same technical or physical effect are usually provided with the same reference numbers or are identified with the same name, so that the description of these elements and of the functionality thereof as illustrated in the different embodiments are mutually exchangeable or may be applied to one another in the different embodiments.

DETAILED DESCRIPTION OF ILLUSTRATIVE EMBODIMENTS

In the following description, embodiments and examples are discussed in detail, however, it should be appreciated that the embodiments and examples provide many applicable concepts that can be embodied in a wide variety of semiconductor devices. The specific embodiments and examples discussed are merely illustrative of specific ways to make and use the present concept, and do not limit the scope of the embodiments. In the following description of embodiments and examples, the same or similar elements having the same function have associated therewith the same reference signs or the same name, and a description of such elements will not be repeated for every embodiment. Moreover, features of the different embodiments described hereinafter may be combined with each other, unless specifically noted otherwise.

It is understood that when an element is referred to as being "connected" or "coupled" to another element, it may be directly connected or coupled to the other element, or intermediate elements may be present. Conversely, when an element is referred to as being "directly" connected to another element, "connected" or "coupled," there are no intermediate elements. Other terms used to describe the relationship between elements should be construed in a similar fashion (e.g., "between" versus "directly between", "adjacent" versus "directly adjacent", and "on" versus "directly on", etc.).

The embodiments shown in the figures are presented with a coordinate system, so that a thickness of the different layers extends along the z-direction, while the extension of the different layers extends parallel to an x-y plane.

Figure 1:
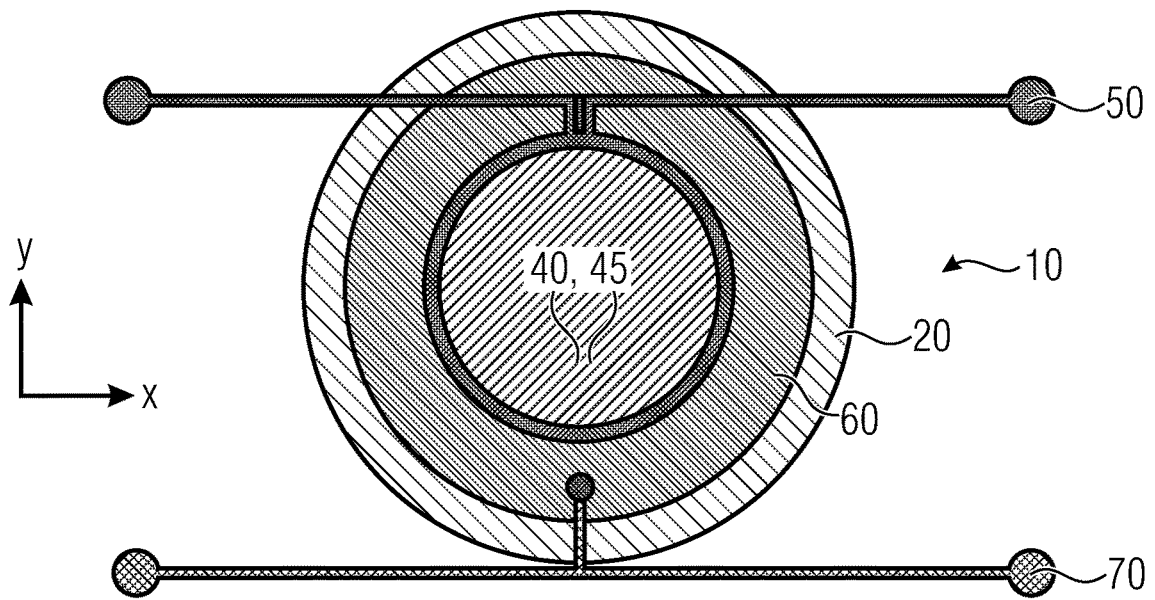
FIG. 1 shows a schematic top view of a gas sensitive device according to an embodiment.
Figure 2:
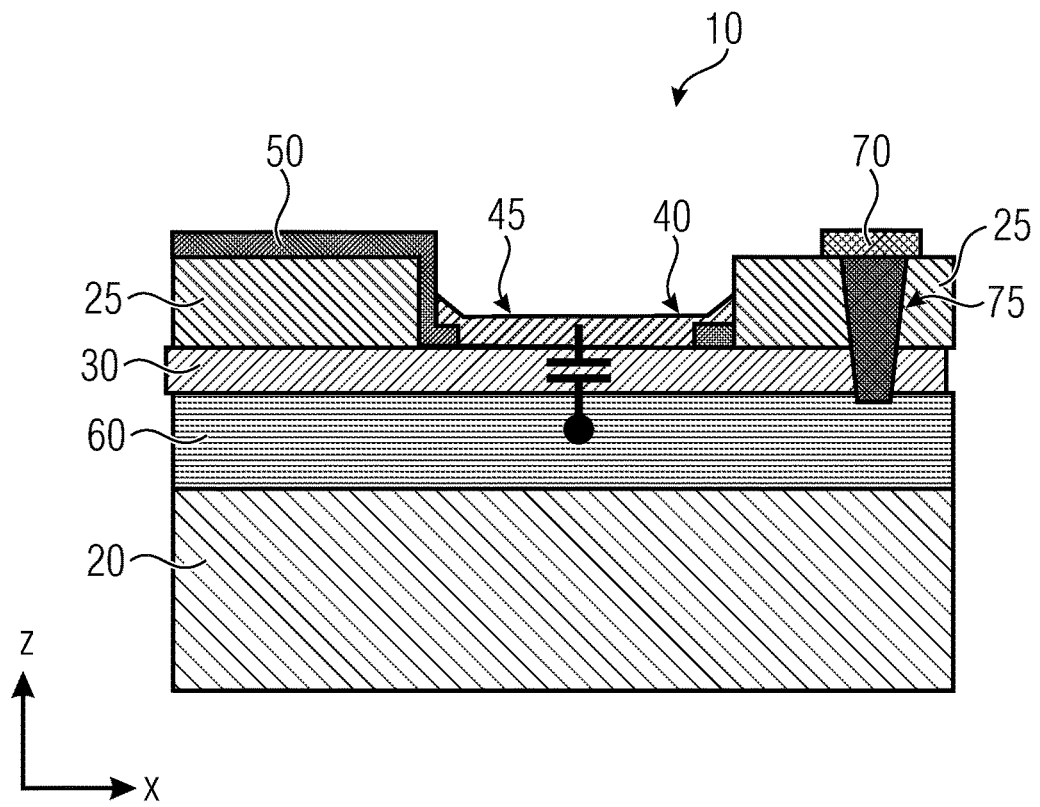
FIG. 2 shows a schematic cross-sectional view of a gas sensitive device according to an embodiment.

FIG. 1 shows a schematic top view of a gas sensitive device 10 according to an embodiment; and FIG. 2 shows a schematic cross-sectional view of the gas sensitive device 10 as shown in FIG. 1. The gas sensitive device 10 comprises a substrate structure 20, and a gas sensitive capacitor. The gas sensitive capacitor comprises a first capacitor electrode 40 in form of a gas-sensitive layer 45 on a first main surface region of an insulation layer 30, and a second capacitor electrode 60 in form of a buried conductive region below the insulation layer 30. The insulation layer 30 is arranged between the first and second capacitor electrode 40, 60. The gas-sensitive layer 45 comprises a sheet resistance or a sheet impedance which changes in response to the adsorption or desorption of gas molecules. The first capacitor electrode 40 may for example be called a top electrode, because it is disposed on top of the gas sensitive device 10. The first capacitor electrode 40 is in contact with the ambient atmosphere allowing for adsorbing or desorbing gas molecules from the ambient atmosphere. The second capacitor electrode 60 is provided directly below the insulation layer 30 or directly below a stack of insulation layers 30 or between a stack of first insulation layers 30 and second insulation layers 35. It is possible that the insulation layer 30 and/or insulation layer 35 comprises a stack of different insulation layers 30, 35. As for example shown in FIG. 2, the second capacitor electrode 60 may be disposed above the substrate structure 20, so that the second capacitor electrode 60 may be in contact on one side with the insulation layer 30 and on the opposite side may be in contact with the substrate structure 20. The first capacitor electrode 40 may be in contact on one side with the insulation layer 30, wherein the insulation layer 30 is a first insulation layer 30. On the opposite side the first capacitor electrode 40 may have an external surface region being in contact with the ambient atmosphere (see FIG. 2). The second capacitor electrode 60 may also be called the buried electrode. For example, the gas sensitive layer 45 may have a thickness along the z-direction depending on the material, and the thickness of the gas sensitive layer 45 can vary over a wide range. A preferred thickness would be in the range of a real two dimensional layer (e.g., a graphene monolayer) up to several nanometers, for example, about 40 nm.

As can be derived from FIG. 1 or FIG. 2, the first capacitor electrode 40 and second capacitor electrode 60 may be provided with contact regions 50, 70. The gas sensitive device 10 comprises a first contact region 50 for electrically contacting the first capacitor electrode 40, and a second contact region 70 for electrically contacting the second capacitor electrode 60. For contacting the second capacitor electrode 60 the gas sensitive device 10 may be provided with a contact hole 75 extending through the gas sensitive device 10 from the second contact region 70 to the second capacitor electrode 60. The insulation layer 30 between the first and second capacitor electrode 40, 60 may be a dielectric material, for example SiN.

In an embodiment, a capacitive gas sensitive device, utilizes a capacitive measurement method between a top and a buried electrode. The top electrode material is the gas sensitive layer 45 (e.g., graphene). The change of adsorbed gas molecules on the top electrode results in a change of the charge carrier density, which leads to a change of the AC impedance behavior.

The embodiment gas sensitive device 10 has an improved product performance expected due to the fact, that the gas detection with the new design will be no longer determined by lumps between the metal finger or the small coffee ring surrounding the sensor field, but by the much more bigger sensor area at the top of the gas sensitive device 10.

Figure 3:
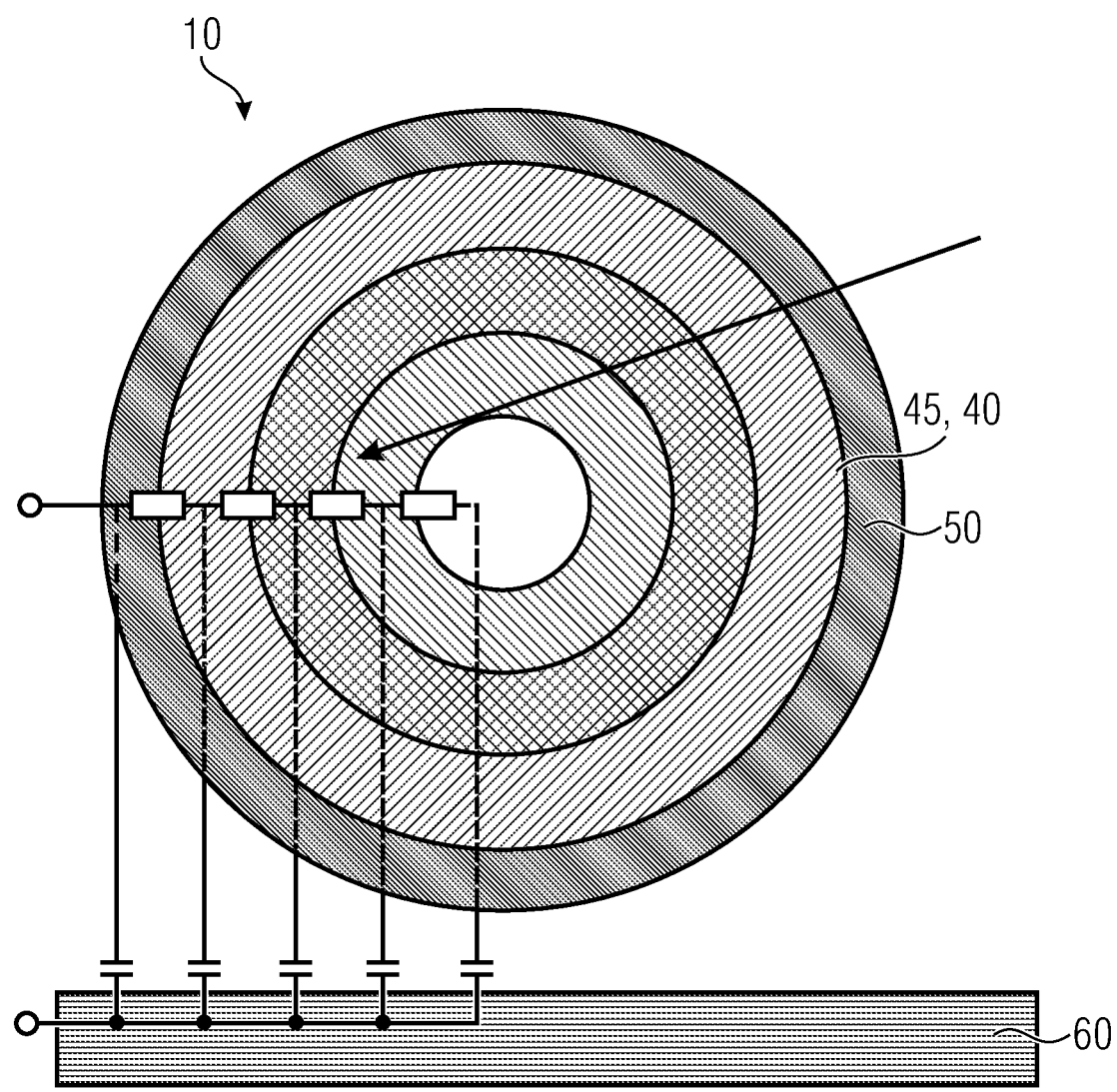
FIG. 3 shows a schematic view of an equivalent circuit of the gas sensitive device according to an embodiment.

FIG. 3 shows a schematic view of an equivalent circuit of the gas sensitive device 10 according to an embodiment. Supposing an AC-coupling of the first capacitor electrode 40, an equivalent circuit may be given by an RC-network. Here, the first contact region 50 is ohmically coupled to the first capacitor electrode 40. Such a RC-network may have a frequency behavior depending in the adsorbed gas molecules. This means the sheet resistance or the sheet impedance of the top electrode or the first capacitor electrode 40 changes by the adsorption or desorption of gas molecules, for example of $NO_2$ (nitrogen dioxide), $O_3$ (ozone) or $C_O$ (carbon monoxide).

Figure 4:
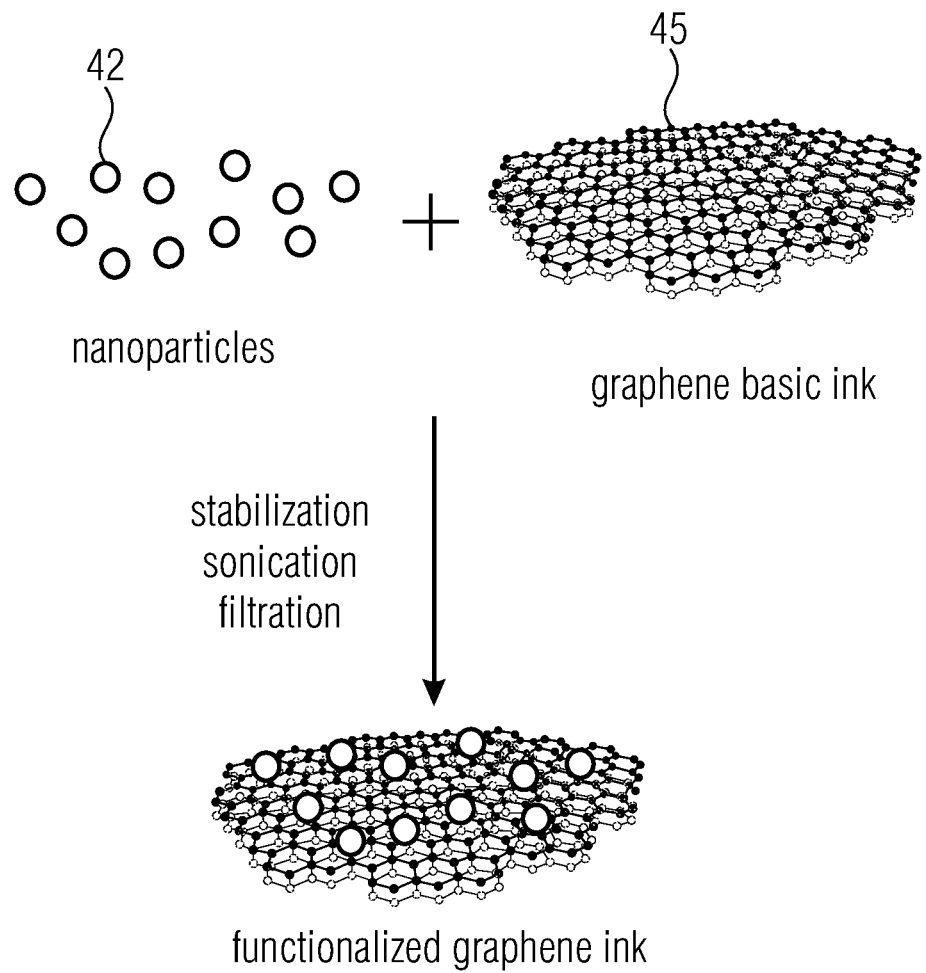
FIG. 4 shows a schematic view of a graphene material.

FIG. 4 shows a schematic view of a graphene material, i.e. the two dimensional structure of the graphene doped with nanomaterials. Graphene is arranged in a two-dimensional honeycomb lattice, which may be doped with nanoparticles 42 or doped with salts. Depending on the chosen nanoparticles 42 or the salts, the graphene may become sensitive for the adsorption of specific gas molecules from the ambient atmosphere. By doping the graphene with nanoparticle and/or with salts the graphene becomes functionalized. The herein disclosed sensor principle also works with a not graphene based gas sensitive layer 45. Subject to the condition, that the used material is showing the described behavior. Examples of not graphene based layers 45 may be an amorphous Carbon, thin poly silicon, tantalnitride, titannitride, AlScN, or every material which forms a thin or two dimensional layer that has an electrical conductivity that can be influenced by the interaction with gas molecules.

Figure 9A:
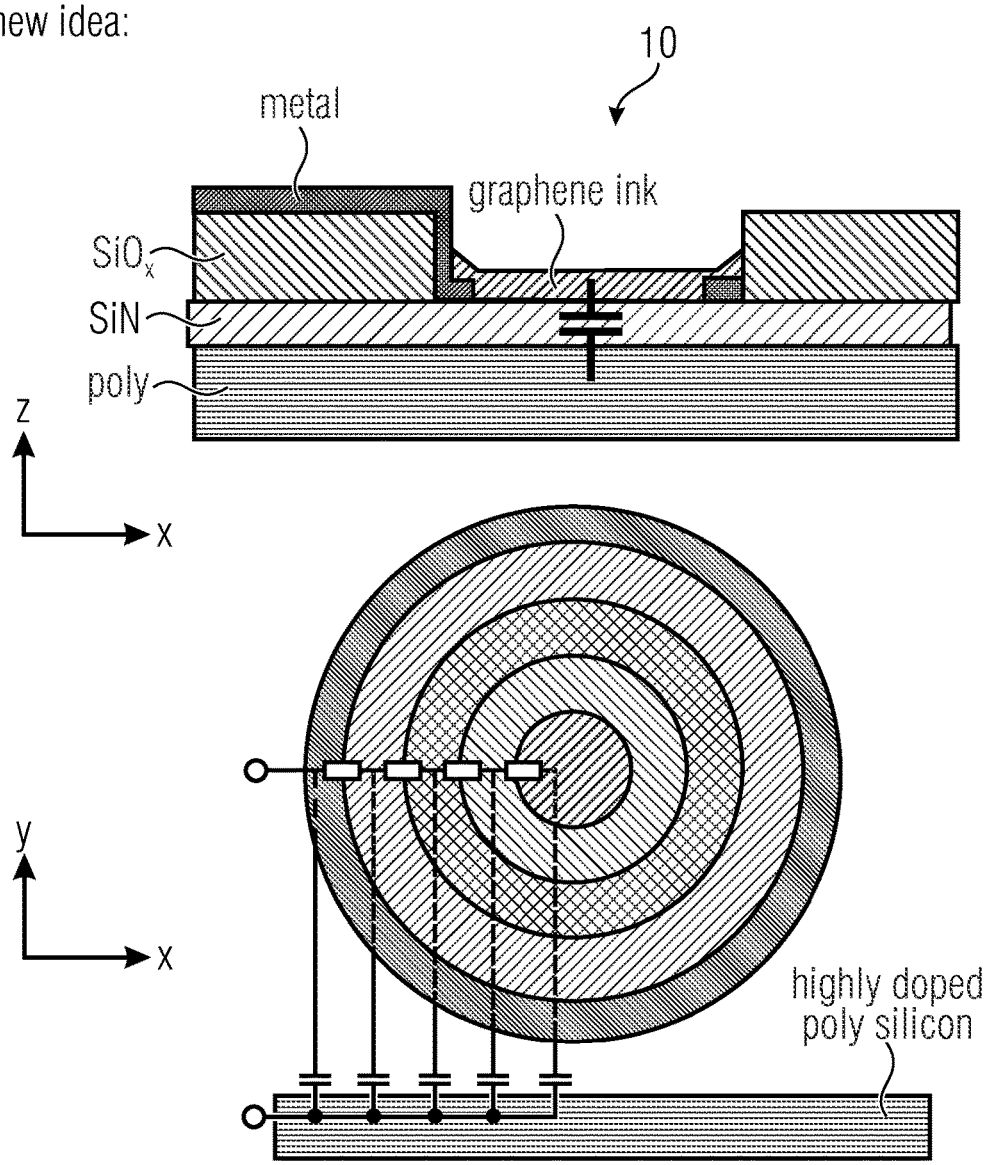

FIGS. 9a and 9b shows a comparison between the proposed gas sensitive device (shown in FIG. 9a) having an AC-coupled sensitive layer versus an established impedance measurement technique (shown in FIG. 9b). For performing the established AC-measurement technique an interdigital structure is necessary. Then a lateral AC measurement can be performed in order to determine the real and the imaginary parts of the impedance Z. The established impedance measurement technique needs the interdigital structure in order to be performable. The proposed gas sensitive device 10, however, has a simple structure and allows also for measuring the impedance.

Figure 10:
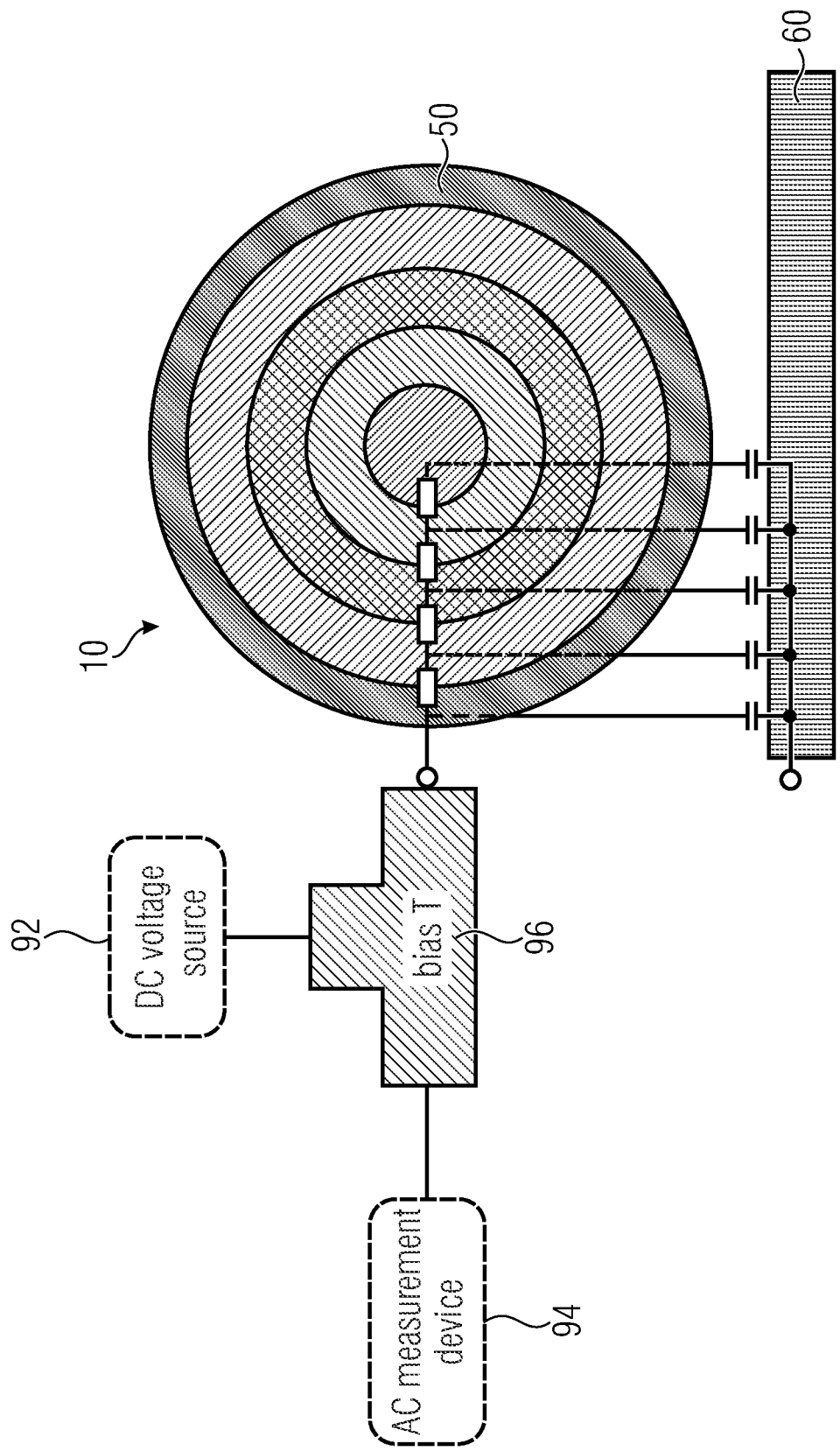
FIG. 10 shows a schematic view of the gas sensitive device coupled to an AC-measurement device and coupled to a DC voltage source.

FIG. 10 shows a schematic view of the gas sensitive device 10 coupled to an AC-measurement device and coupled to a DC voltage source. A sensitivity of the proposed gas sensitive device 10 can be adjusted by applying and adjusting a DC bias voltage VDC-bias. For doing so, the gas sensitive device 10 is connected with a DC voltage source 92 and with an AC measurement device 94 vie a bias T-component 96.

Figure 11:
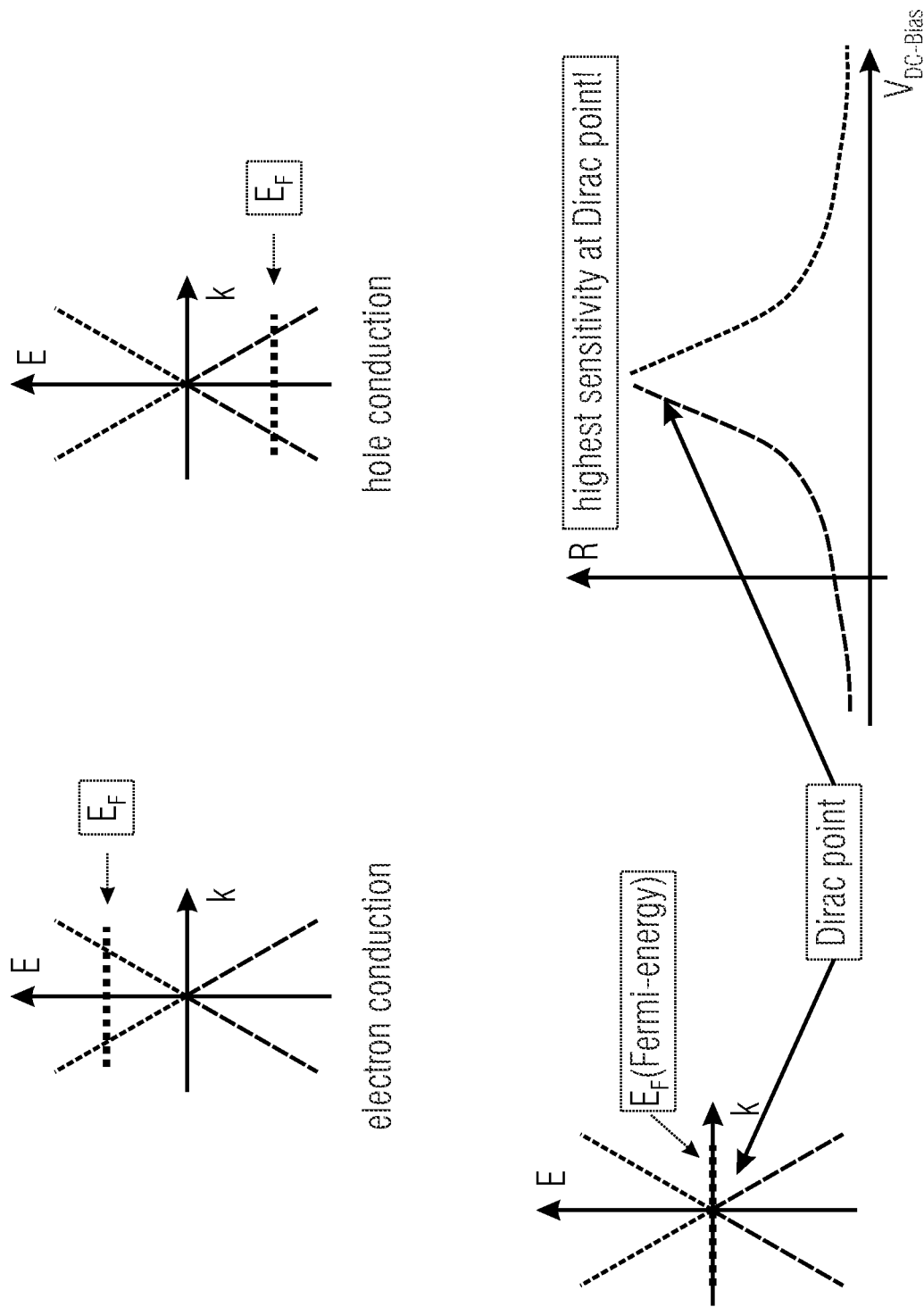
FIG. 11 shows a theoretic explanation of the graphene band-structure.

FIG. 11 shows a theoretic explanation of the graphene band-structure. FIG. 11 also shows schematically the effect of adjusting the DC bias voltage until the so called "Dirac point" is reached. Depending on the position of Fermi's energy EF the graphene provides electron conduction or provides hole conduction. It was found that at the Dirac point the gas sensitive layer has its highest sensitivity for adsorbing gas molecules from the ambient atmosphere. It should be noted that the "Dirac point" is influenced by the functionalization of the gas sensitive layer 45, the (target) gas concentration and/or temperature. By using one or all of the parameters the regime at which the gas sensitive devices are sensitive or have a maximum sensitivity to ambient gases can be identified and, thus, can used for detecting gas molecules in the ambient atmosphere. The Dirac point of the gas sensitive device 10 can be determined from the local maximum of the DC-bias voltage VDC-Bias versus the resistance R.

Figure 12:
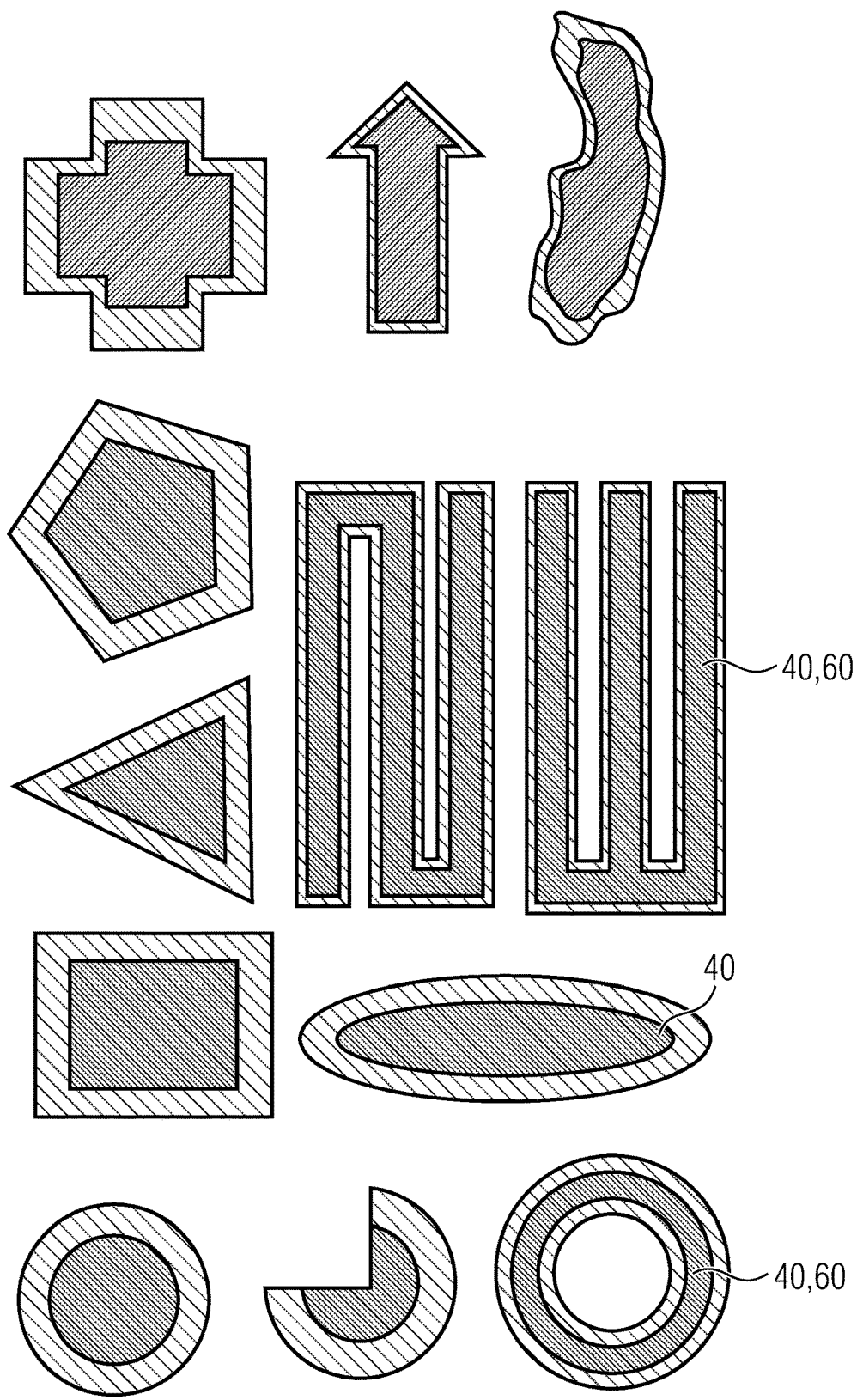
FIG. 12 shows possible design variants for the gas sensitive area of the gas-sensitive device.

FIG. 12 and FIG. 13 show possible design variants for the gas sensitive area of the gas-sensitive device 10. For example, a projection of the first capacitor electrode 40 vertically with respect to the first main surface region at least partially or completely overlaps with the second capacitor electrode 60. The FIG. 12 and FIG. 13 show for example that different kinds of circle or parts of circles are possible to choose for the first and/or second capacitor electrodes 40, 60. Furthermore the first and/or second capacitor electrodes 40, 60 may be formed, for example, as ellipses or parts of ellipses, polygons or part of polygons, meander or parts of meander, combs or parts of a comb. It is also possible to choose a combination of different geometries or a combination of different shapes. Also, a free hand designed shape may be chosen (see FIG. 12). Also, a different overlap sensing area to the underlying substrate structure 20 may be chosen (see FIG. 13).

FIG. 13 also shows that a surrounding shape of the first electrode 40 may be different from a surrounding shape of the insulator layer 30 or wherein a surrounding shape of the first electrode 40 may be equal to a surrounding of the insulator layer 30. If different surrounding shapes of the insulator layer 30 and the first electrode 40 a partial overlap may result (FIG. 13*f*). Also, a complete overlap may result according to the example shown in FIG. 13*e,* when different surrounding shapes of the insulator layer 30 and the first electrode 40 are used. Different configurations in which surrounding shape of the first electrode 40 may be equal to a surrounding of the insulator layer 30 are shown in FIGS. 13*a* to 13*d*. As shown in FIG. 13, the first electrode 40 completely or only partially overlaps the surface of the insulator layer 30. The insulator layer can be made of SiN and can have a thickness along the z-direction of about 150 nm to 200 nm. The insulator layer 30 can also be made of other dielectrics or can be made of a stack of different dielectrics, for example SiN/SiO/SiN or the like. The person skilled in the art is conscious about the correct molecule formula of SiO and $Si_yN_x$, which are here abbreviated with SiO and SiN, respectively.

According to an embodiment, the first contact region 50 at least partially or completely surrounds and electrically contacts the first capacitor electrode 40. Thereby, the first contact region 50 forms an area contact region or a point contact region with the first capacitor electrode 40. The same may apply to the second contact region 70, i.e. the second contact region 70 forms an area contact region or a point contact region with the second capacitor electrode 60 or with the second and a third capacitor electrode 60, 65. As shown in FIG. 14*a,* the first contact region 50 may be a full contact, surrounding fully or completely the gas sensitive layer 45. Also, the first contact region 50 may be a partial contact, only partially surrounding the gas sensitive layer 45 (FIG. 14*b*). Furthermore, the first contact region 50 may an area contact, having an area that is in contact with or next to the gas sensitive layer 45 (FIG. 14*c*). Furthermore, the first contact region 50 may be generated by a point contact, wherein only a point is in contact with the gas sensitive layer 45 (FIG. 14*d*). Furthermore, the first contact region 50 may be generated by any combination of the disclosed different kinds of contact (FIG. 14*e*). The disclosed example of the different contact regions, as shown on FIG. 14 may be used for the first capacitor electrode 40 and/or for the second capacitor electrode 60. The contact region 50 may be made of a metal or any other electrically conducting material.

According to an embodiment, on top of the insulation layer 30 a cover layer 25 is disposed. The cover layer 25 has at least a common plane with the first contact region 50 and/or with the first capacitor electrode 40, so that the cover layer 25 surrounds the first contact region 50 or the first contract region 50 and the first capacitor electrode 40 in the at least one common plane. Such embodiments are, for example, shown in FIGS. 2, 6, 16, 17 and 18. Stated differently, along the x-direction the cover layer 25 and at least the first contract region 50 and the first capacitor electrode 40 share a common plane, i.e. the cover layer 25 and at least the first contract region 50 and the first capacitor electrode 40 lie in the same common plane(s).

According to an embodiment, the first contact region 50 extends from the first capacitor electrode 40 in the at least one common plane to a position above the cover layer 25 being in at least a plane parallel to the at least one common plane. As for example, shown in the FIGS. 2, 6, 16, 17 and 18, starting from the first capacitor electrode 40 the first contact region 50 contacts a first border region of the first capacitor electrode and extends along the −x direction (here the contact region extends on top of the insulation layer 30 in −x direction). Then first contact region 50 extends along the z direction and then along again the −x direction, i.e. the first contact region 50 extends on top or above the cover layer 25. The extension along the z direction corresponds to a thickness of the cover layer 25 along the z-direction. FIGS. 2, 6, 17, 17 and 18 for example, show that the first border region of the first capacitor electrode 40 has a sloped curvature (i.e., is ramped) along x-z-direction.

All disclosed different kinds of first contact regions 50 have in common that the first contact region 50 ohmically contacts a first border region of the first capacitor electrode 40, in particular the gas sensitive layer 45 of the top electrode. As shown in FIG. 14, the first contact region 50 contacts the first border region of the first capacitor electrode 40 directly.

As shown in FIG. 15 the second buried capacitor electrode 60 may capacitively contact a center region of the first capacitor electrode 40. Also, the buried third capacitor electrode 65 may capacitively contact a second border region of the first second capacitor electrode o. The second and third capacitor electrodes contact regions 60, 65 may be given by different kinds of partial contact, point contact or any combination of different contact form with the first capacitor electrode 40, i.e. the gas sensitive layer 45. For example, the first capacitor electrode 40 may be given as a rectangle or square, as an ellipse or circle or any other geometry.

Figure 5:
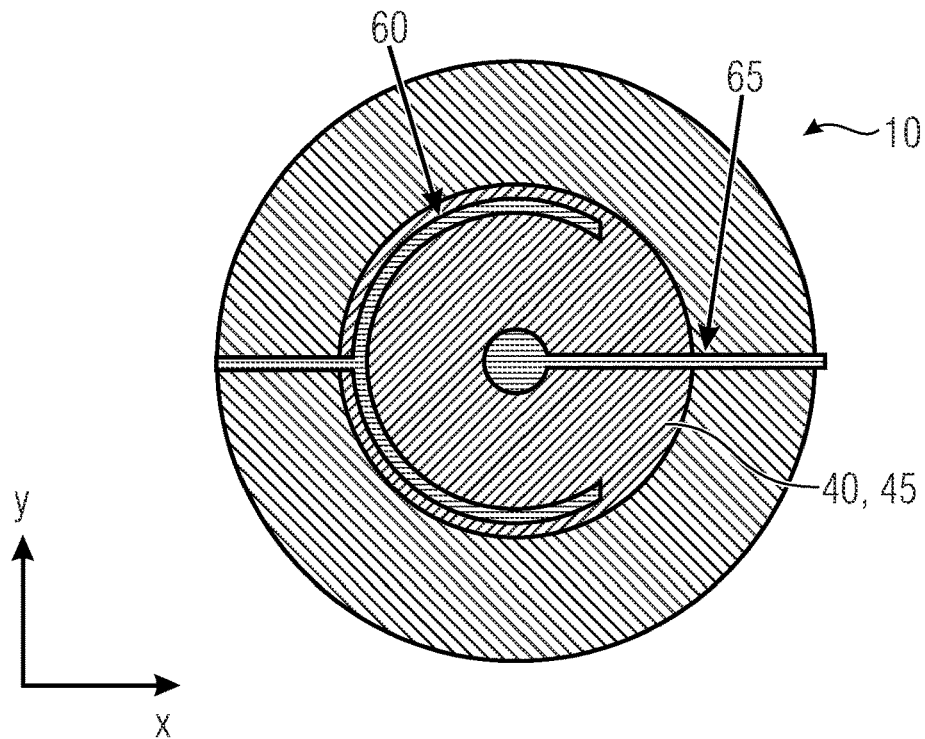
FIG. 5 shows a schematic top view of a gas sensitive device according to an embodiment.
Figure 6:
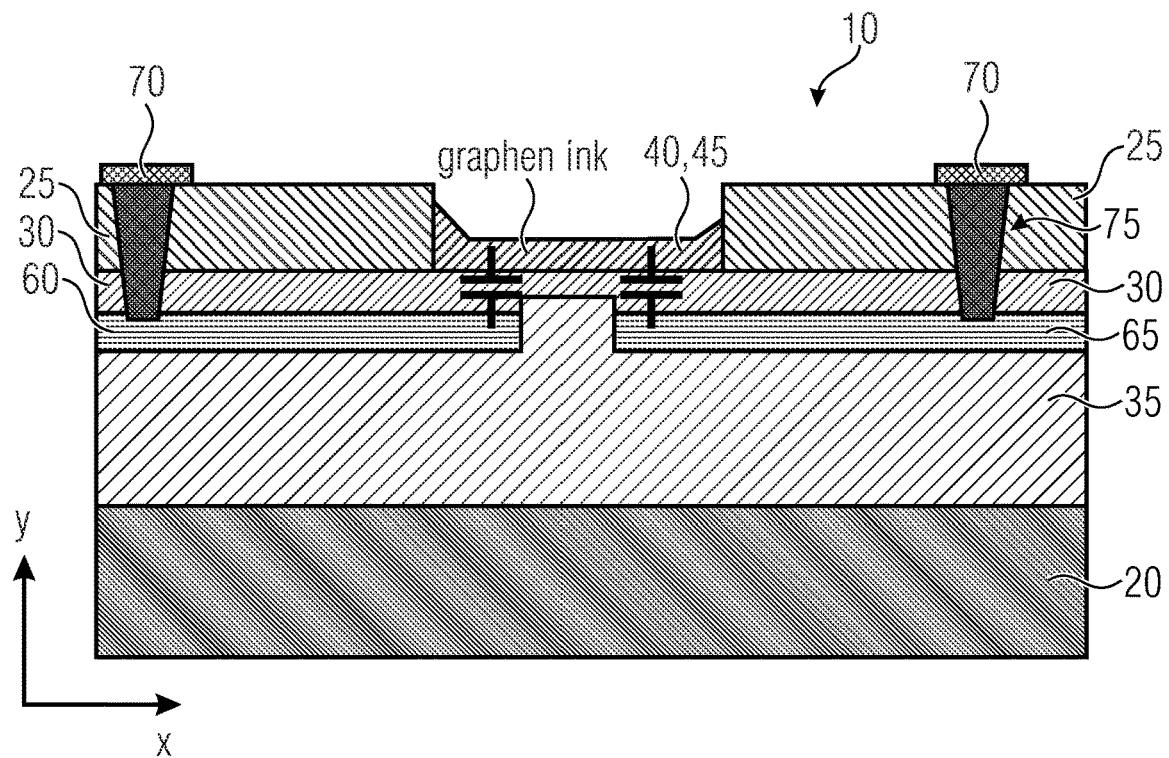
FIG. 6 shows a schematic cross-sectional view of a gas sensitive device according to an embodiment.

According to a different implementation of the same concept as proposed herein FIG. 5 and FIG. 6 show a further embodiment. As shown in FIG. 5 and FIG. 6, the capacitor electrode 40 is capacitively contacted by the second capacitor electrode 60 and the third capacitor electrode 65, i.e. by the two buried electrodes 60, 65. The buried second capacitor electrode 60 and the buried third capacitor electrode 65 are arranged in the same plane of the gas sensitive device 10. The second contact region 70 is coupled to the second capacitor electrode 60 or to the second and third capacitor electrodes 60, 65. The second contact region 70 and the second capacitor electrode 60 may be arranged in the same plane or in different planes of the gas sensitive device. Preferably, if the second contact region 70 and the second capacitor electrode 60 or the second and third capacitor electrodes 60, 65 are arranged in different planes of the gas sensitive device 10, these planes are parallel to each other. As shown in FIG. 6 the second and the third capacitor electrodes 60, 65 are separated along the x-y-directions by a second insulation layer 35 extending between the third capacitor electrode 65 and the second capacitor electrode 60.

FIGS. 15*a* to 15*g* show variations of the implementation of the gas sensitive device 10 as shown in FIG. 5 and FIG. 6. The variations as shown in FIG. 15 show two buried electrodes 60, 65, i.e. the second capacitor electrode 60 and the third capacitor electrode 65, which may have the same or a different geometry to each other. For example, FIGS. 15*a,* 15*c,* and FIG. 15*e* show implementations in which the second capacitor electrode 60 has a different geometry or shape from the third capacitor electrode. For example, FIGS. 15b, 15d, 15f and FIG. 15g show in which the second capacitor electrode 60 and the third capacitor electrode have the same geometry or shape, the shapes are only mirrored along an y-axis, said y-axis is located in the middle between the both electrodes 60, 65. In all implementations, the two buried electrodes 60, 65 may have a line shape or a line shape combined with a point shape or any circle shape or any circle shape combined with a point shape, wherein the circle shape may comprise a full circle or any sub-circle shape.

FIG. 7 shows a schematic view of a gas sensitive device 10 and of an equivalent circuit of an AC-coupled multi gas sensor 1000 comprising four gas sensitive devices 10 according to an embodiment. The configuration of the gas sensitive device 10 is already described with reference to FIGS. 1 and 2. As shown in FIG. 7, an equivalent circuit of the AC-coupled multi-gas sensor 1000 is given by a RC-network. The sheet resistance is depending on the gas sensitive layer 45, in particular depending on the graphene layer. However, the resulting adsorption of gas molecules depends on the presence of the according gas molecules and the level of doping with nanoparticles or salts. Different chip layouts may be used for high frequency measurements or for low frequency measurements. For high frequency measurements, which are also called high frequency NWA measurement, the amount a connections are higher than the connections used in the low frequency lock-in measurement technique. For example, for the low frequency lock-in measurement technique each first capacity electrode 40 of each gas sensitive device 10 has one connection to an outer port 101, while each of the second capacitor electrode 60 of the gas sensitive device 10 has a common single connection to an outer port. This is different to the high frequency NWA measurement technique, where each of the first capacity electrodes 40 of each gas sensitive device 10 and each of the second capacity electrodes 40 of each gas sensitive device 10 has two connections to an outer port 101. This means each gas sensitive device 10 has four connections to outer ports, two gate-ports and two source ports. The four connections to outer ports enable a 2-Port NWA-measurement in „T-configuration", which neglects the impedances of the connection lines. Preferably, the first capacity electrodes 40 are connected to the first port and the second capacity electrodes 60 are connected to the second port. For such a configuration the following equations are valid:

$$Z_{11} = \frac{U_1}{I_1}\bigg|_{I_2=0} = Z_1 + Z_3$$

$$Z_{21} = \frac{U_2}{I_1}\bigg|_{I_2=0} = Z_3$$

$$Z_{22} = \frac{U_2}{I_2}\bigg|_{I_1=0} = Z_2 + Z_3$$

$$Z_{12} = \frac{U_1}{I_2}\bigg|_{I_1=0} = Z_3$$

Here U is the voltage, I the current and Z the impedance. The indices give the current, voltage and impedance according to the elements of the circuit shown in FIG. 7. In detail, Z3 is the impedance of the gas sensitive capacitor without any parasitics, Z1 and Z2 are the (parasitic) impedances of the connecting lines. The switching frequency is determined by the sheet resistance of the gas sensitive layer 45 and therefore by the adsorbed gas molecules. At low frequencies the sheet resistance of the sensitive layer is directly reflected in the real part of impedance. The gas sensitive capacitor enables different AC measurement capabilities (e.g., Lock-in technic, PPL, S-Parameter, as shown in FIG. 7). Compared to simple DC-resistance measurements, one of the advantages of AC-measurement methods is noise reduction. Furthermore, AC-measurement allows distinguishing between real and imagery impedance of the gas sensitive layer 45 and delivers therefore more information.

According to an embodiment, the first main surface region of the insulation layer 30 having the gas-sensitive layer 45 is topology-free. For example, the gas sensitive layer 45 is manufactured by dropping an ink drop onto the insulation layer 30. Because the gas-sensitive layer 45 according to the present disclosure has no topology, the influence of locally clustered graphene flakes and/or from coffee stain does not affect the gas-sensitive layer 45. The topology-freeness of the gas-sensitive layer 45 is shown throughout the figures except FIGS. 4, 8, 11 and 20.

According to an embodiment, the first capacitor electrode 40 and the second capacitor electrode 60 are arranged parallel to each other and vertical with respect to the first main surface region of the insulation layer 30. With respect to the figure, where a gas sensitive device 10 is shown the first capacitor electrode 40 and the second capacitor electrode 60 are each arranged in parallel x-y planes, i.e. horizontal planes. Vertical means here along a z-direction. The insulation layer 30 between the first capacitor electrode 40 and the second capacitor electrode 60 is also called the first insulation layer 30.

According to an embodiment, a third capacitor electrode 65 is disposed apart from the second capacitor electrode 60, wherein the third capacitor electrode 65 and the second capacitor electrode 60 are positioned so that both extend along in at least one common plane. FIG. 6, for example, shows a gas sensitive device 10 having the second and the third capacitor electrodes 60, 65 lying on top of a second insulation layer 35. On top of the cover layer 25 a contact region 70 for the second capacitor electrode 60 and a contact 70 for the third capacitor electrode 65 is disposed. For contacting the second and the third electrode 60, 65 contact holes 75 are provided. The contact holes 75 are, for example, etched. The contact holes 75 extend along the z-direction through the cover layer 25 and through the insulation layer 30.

According to an embodiment, the third capacitor electrode 65 and the second capacitor electrode 60 are spaced apart from each other in the least one common plane by the second insulation layer 35 extending between third capacitor electrode 65 and the second capacitor electrode 60. The third capacitor electrode 65 and the second capacitor electrode 60 are spaced apart from each other by a part of the second insulation layer 35 extending between the third capacitor electrode 65 and the second capacitor electrode 60 along the z-direction. As shown in FIG. 6, the second and the third capacitor electrodes 60, 65 are sandwiched between the first insulation layer 30 and the second insulation layer 35.

According to an embodiment, the first capacitor electrode 40 being the gas sensitive layer 45 is a thin and/or two-dimensional layer 45, the electrical conductivity of which is influenceable by an interaction with gas molecules. For example, the two-dimensional layer 45 may be a conductive graphene based layer. Graphene has a two-dimensional structure as shown in FIG. 4. The two-dimensional structure comprises benzene rings, which may be doped with salts and/or nanoparticles 42. The first capacitor electrode 40 may also be a not graphene based gas sensitive layer 45. Subject to the condition, that the used material is showing the described behavior. Examples of not graphene based layers 45 may be an amorphous Carbon, thin poly silicon, tantalnitride, titannitride, AlScN, or every material which forms a thin or two dimensional layer, which electrical conductivity can be influenced by the interaction with gas molecules.

According to an embodiment, the gas sensitive layer 45 or the thin and/or two-dimensional layer 45, in particular a conductive graphene based layer, is doped with nanoparticles and/or doped with salts for functionalizing the first electrode 40. A concentration of the doped nanoparticle or of the salts correlates to a concentration accuracy with which the adsorbed gas molecules can be measured. The nanoparticle and/or the salt used for doping determine which gas may be adsorbed. Stated differently, by changing the dopant another gas may be detectable.

Figure 16A:
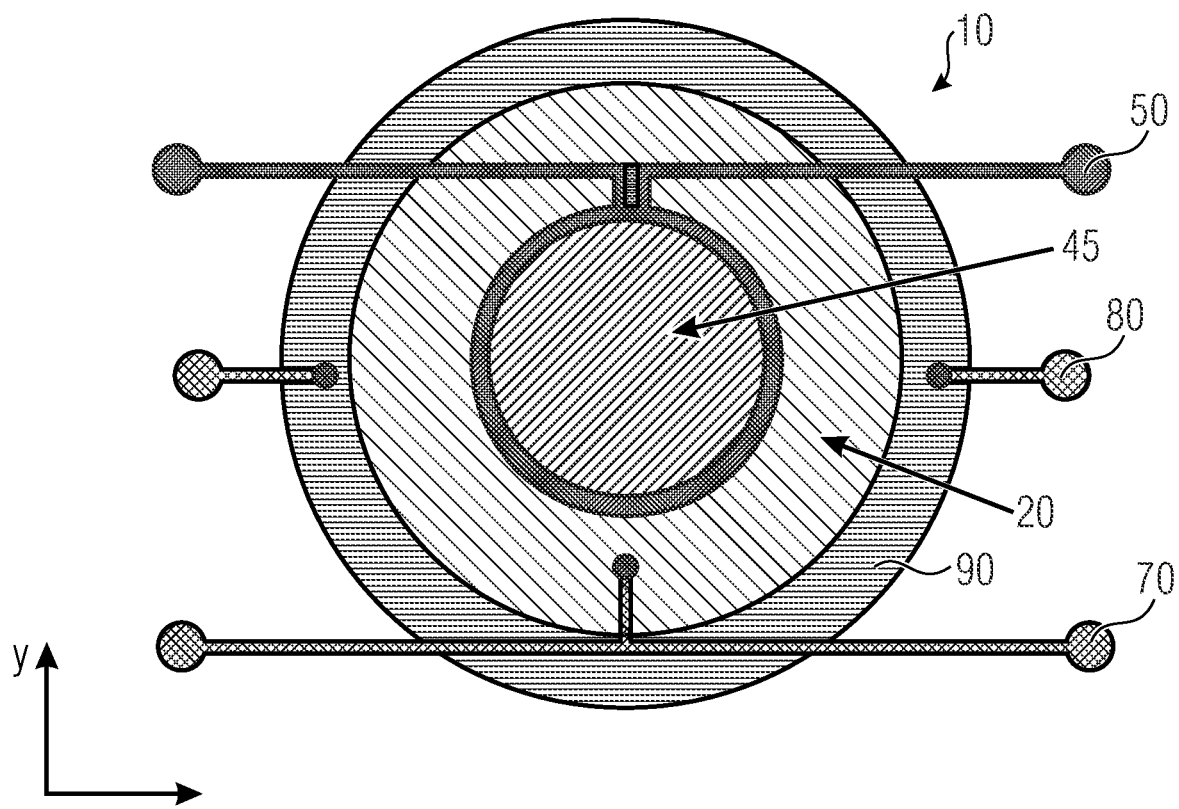
FIG. 16a shows a schematic top view of a gas sensitive device according to an embodiment.
Figure 16B:
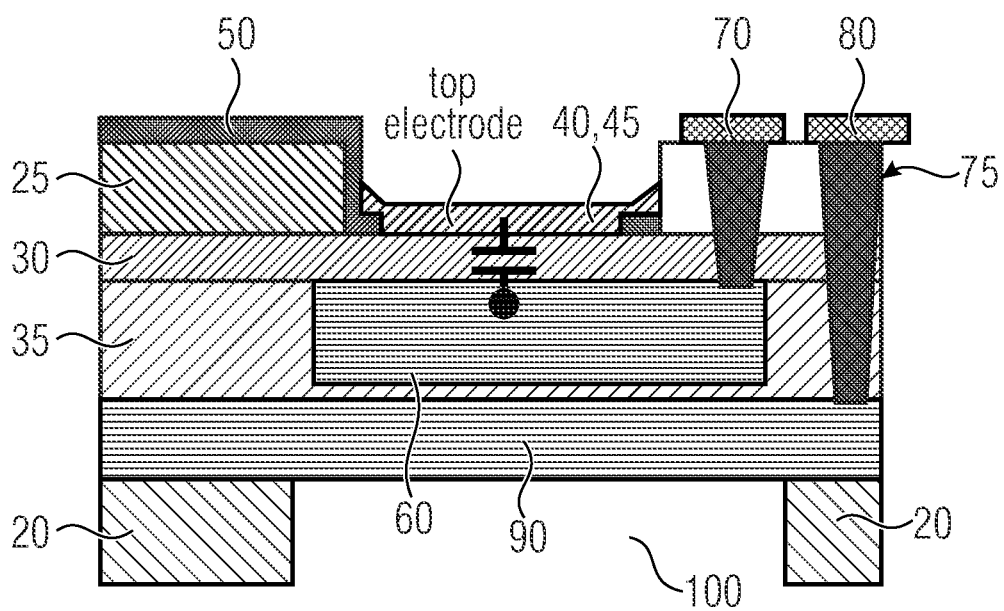
FIG. 16b shows a schematic cross sectional view of a gas sensitive device according to an embodiment (FIG. 16b), both according to an embodiment.
Figure 17A:
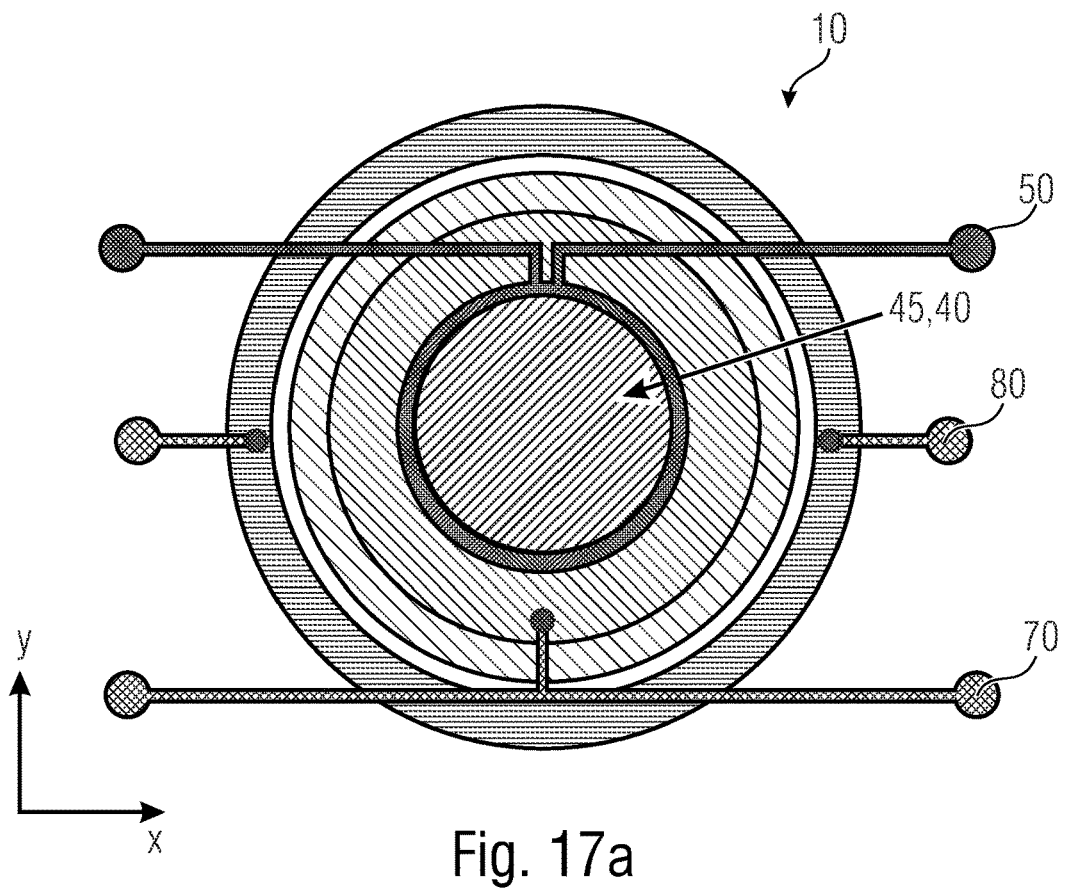
FIG. 17a shows a schematic top view of a gas sensitive device according to an embodiment and FIG. 17b shows a schematic cross-sectional view of a gas sensitive device according to an embodiment, both according to an embodiment.
Figure 17B:
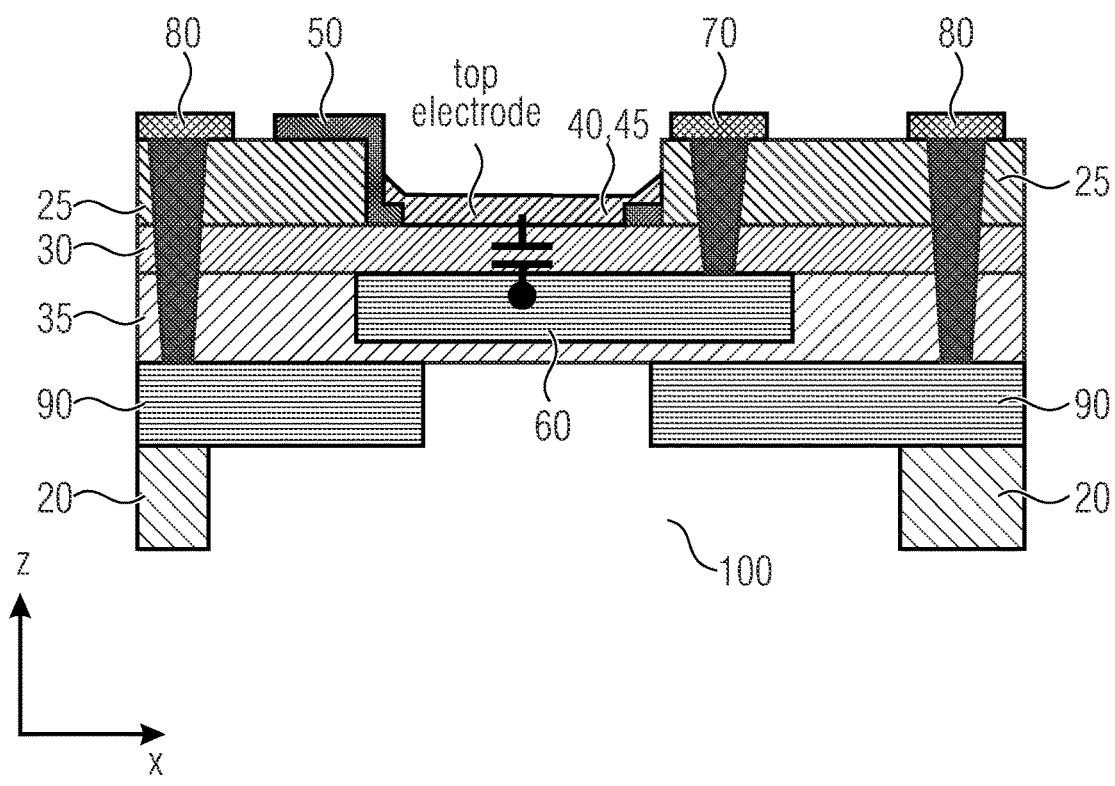
Figure 18A:
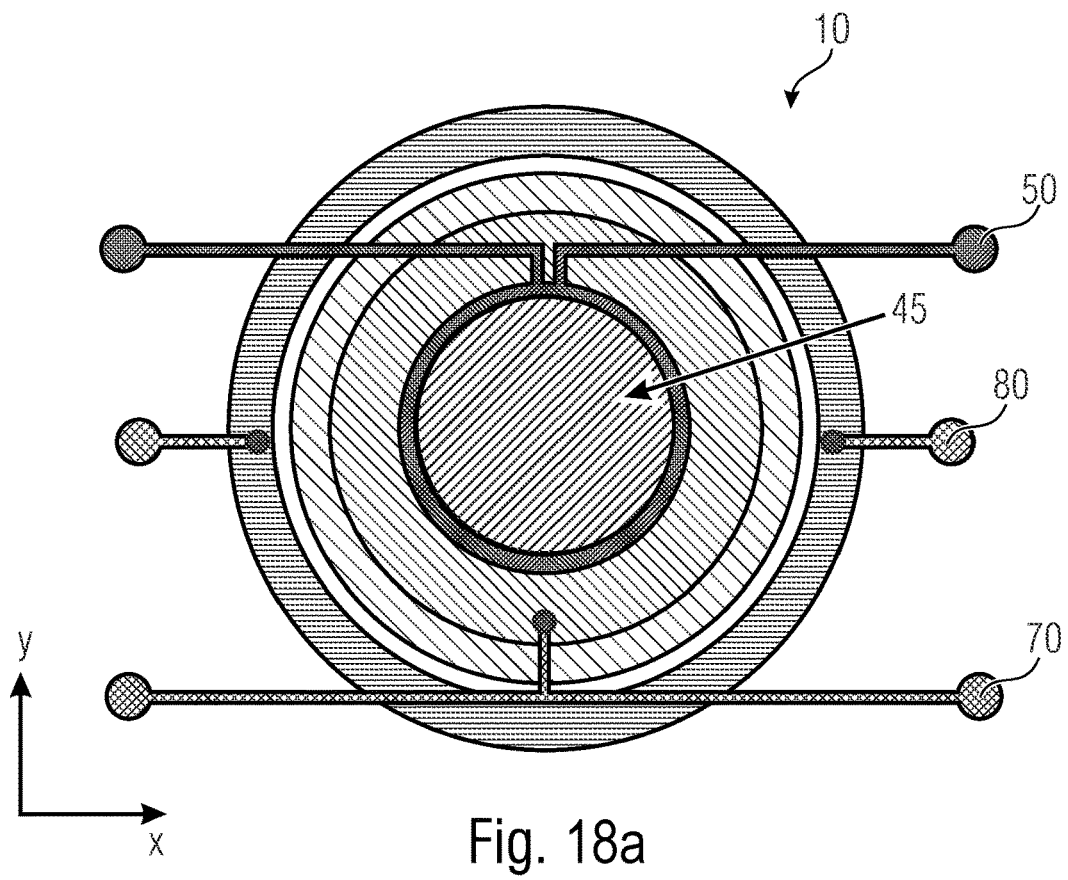
FIG. 18a shows a schematic top view of a gas sensitive device according to an embodiment and FIG. 18b shows a schematic cross-sectional view of a gas sensitive device according to an embodiment, both according to an embodiment.
Figure 18B:
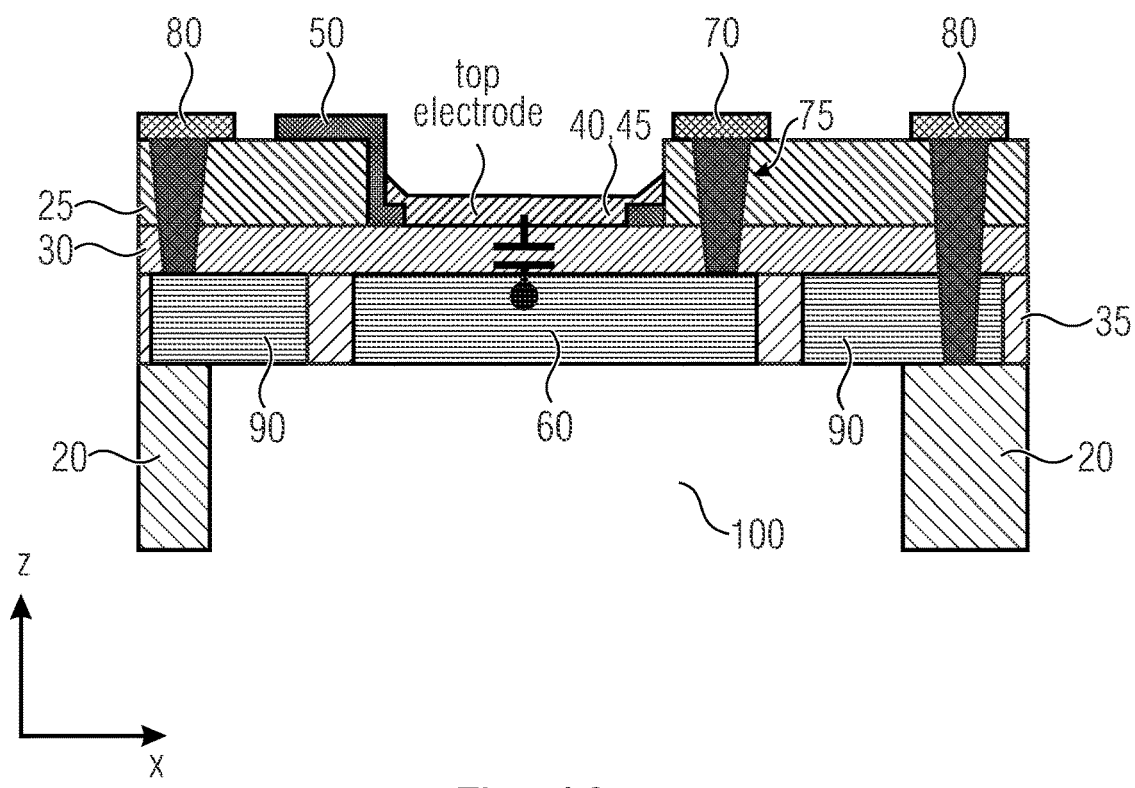

According to an embodiment, the gas sensitive device 10 comprises a heater 90 disposed or positioned in the gas sensitive device 10. The heater is used for bringing the gas-sensitive layer 45 to a desired temperature or temperature profile for sensing, or for resetting the gas-sensitive layer 45. The heater 90 and the second capacitor electrode 60 are separated from each other by the second insulation layer 35. The gas sensitive device 10 comprises a third contact region 80 for electrically contacting the heater 90, as for example shown in FIGS. 16a, 16b, 17a, 17b, 18a or 18b. The heater 90 can be used for resetting or cleaning the gas sensitive layer 45. Cleaning or resetting means in this context to undo the adsorption of the gas molecules. The heater 90 comprises at least one side that at least partially forms with at least a side of the substrate layer 20 a cavity 100, as for example shown in FIG. 16b. FIGS. 17b and 18b show further examples of the cavity 100. In FIG. 17b, for example, the cavity 100 comprises at least one side of the substrate structure 20, at least one side of the heater 90 and at least one side of the second insulation layer 35. In FIG. 18b, for example, the cavity 100 comprises at least one side of the substrate structure 20, at least one side of the heater 90, at least one side of the second insulation layer 35 and at least one side of the second capacitor electrode 60. The cavity 100 is provided for thermal decoupling. In order to keep the necessary heating power small, to reach a target temperature. In FIGS. 16a and 16b, for example, the cavity 100 is shown.

FIGS. 16a, 16b, 17a, 17b, 18a and 18b show different possible examples of where the heater 90 may be located in the gas sensitive device 10. A layout of the heater 90 can deviate from the examples as shown in the figures, in particular the heater 90 may have different geometries. For example, FIGS. 16a, 16b, 17a and 17b show that the heater 90 is located below the second capacity electrode 60. According to FIGS. 16a and 16b, the heater 90 extends in an x-y plane parallel to the second capacity electrode 60. The heater 90 is at least as long and as broad as the second capacity electrode 60. Stated differently, a diameter of the heater 90 in the x-y plane is either as large as or even larger than a diameter of the second capacity electrode 60. According to FIGS. 17a and 17b, the heater 90 extends also in an x-y plane parallel to the second capacity electrode 60. However, the heater 90 forms a ring around the buried electrode. An inner perimeter of the heater ring is preferably larger than an outer perimeter of the buried electrode 60. Stated differently, the heater-ring 90 does not contact the buried electrode 60. In the cross section as shown in FIG. 17b the heater-ring seems like an interrupted heater structure. In the cross-sectional view of FIG. 17b, a length of the heater, in particular in the x-y plane, may be shorter than a length of the buried electrode. Furthermore, the heater 90 is not directly located beneath the second capacity electrode 60. Instead, the heater 90 and the second capacity electrode 60 build a kind of a chessboard pattern with the substrate structure 20. According to FIGS. 18a and 18b, the heater 90 is again formed as a ring and surrounds the second capacity electrode 60, i.e. the heater 90 and the second capacity electrode 60 are disposed in the same plane. Other constructions or any combination of the shown examples are also possible. As shown in FIGS. 16a, 16b, 17a, 17b, 18a and 18b, the heater 90 and the buried electrode 60 may be electrically separated by the insulator layer 30 or 35, for example by SiO or SiN.

According to an embodiment, the gas sensitive device 10 may be provided with a plurality of first electrodes 40 on top of the insulator layer 30 and/or may be provided with a plurality of second electrodes 60 below the insulator layer 30. Of course, the gas sensitive device 10 may also be provided with both, a plurality of first and second contact regions 50, 70. For the sake of simplicity, however, the figures except FIGS. 4, 8a-8d, 11 and 20 of the present application only show a single first contact region 50 and a single second contact region 70.

Figure 19:
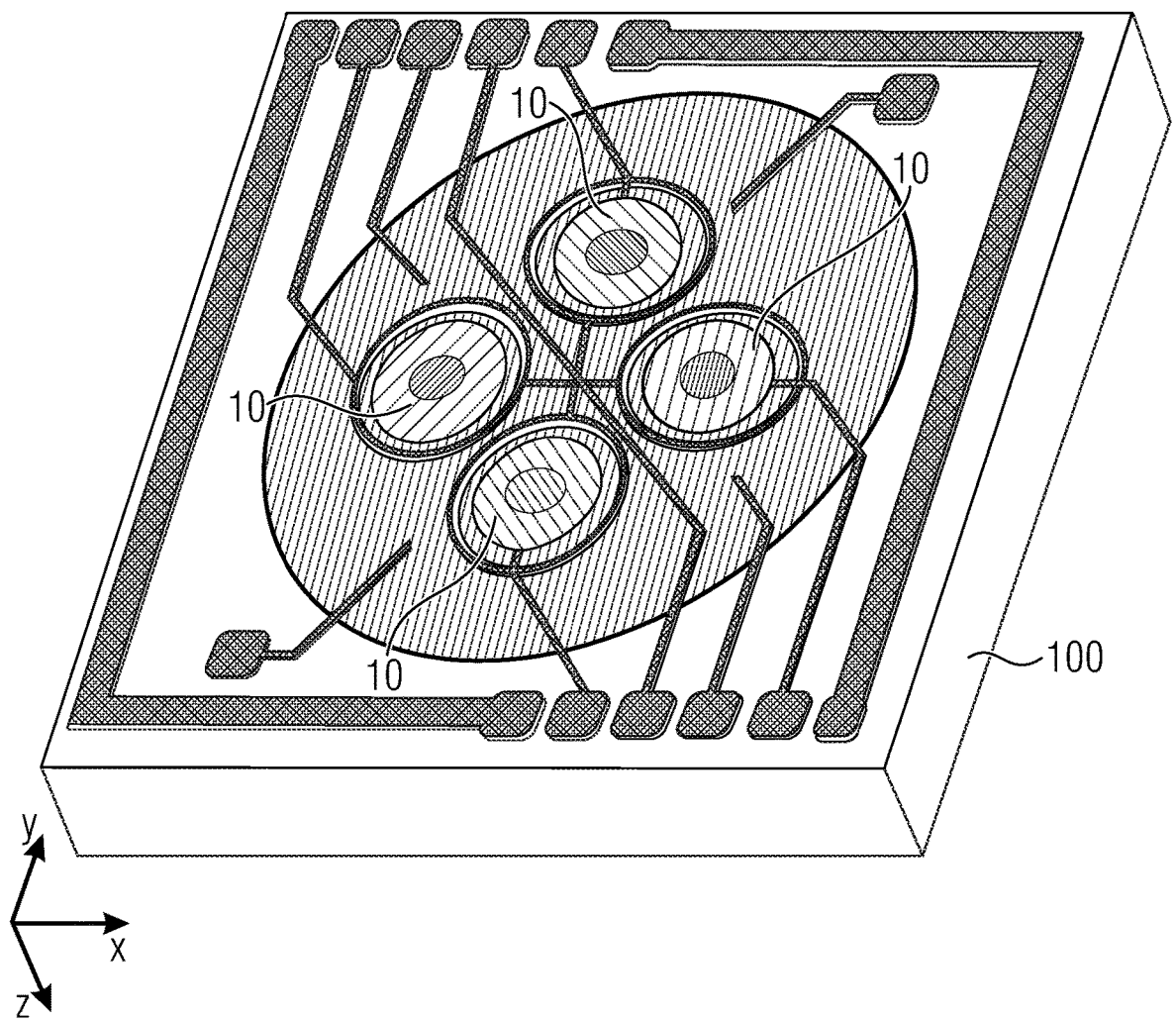
FIG. 19 shows an exemplary embodiment of a multi-gas sensor comprising several gas sensitive devices according to an embodiment.

According to another aspect of the present disclosure a multi-gas sensor 1000 is proposed. The multi-gas sensor comprises two or more gas sensitive devices 10 as disclosed herein. FIG. 19 shows an exemplary embodiment of a multi-gas sensor 1000. The multi-gas sensor 1000 shown in FIG. 19 for example is provided with four gas sensitive devices 10. Each of the gas sensitive devices 10 may be provided with a graphene layer or gas sensitive layer 45 that may be doped with different kinds of nanoparticles and/or salts. In this way, the multi-gas sensor 1000 may become sensitive to the detection of different gas molecules and/or may become sensitive to different kinds of concentration levels of a particular gas molecule.

Figure 20:
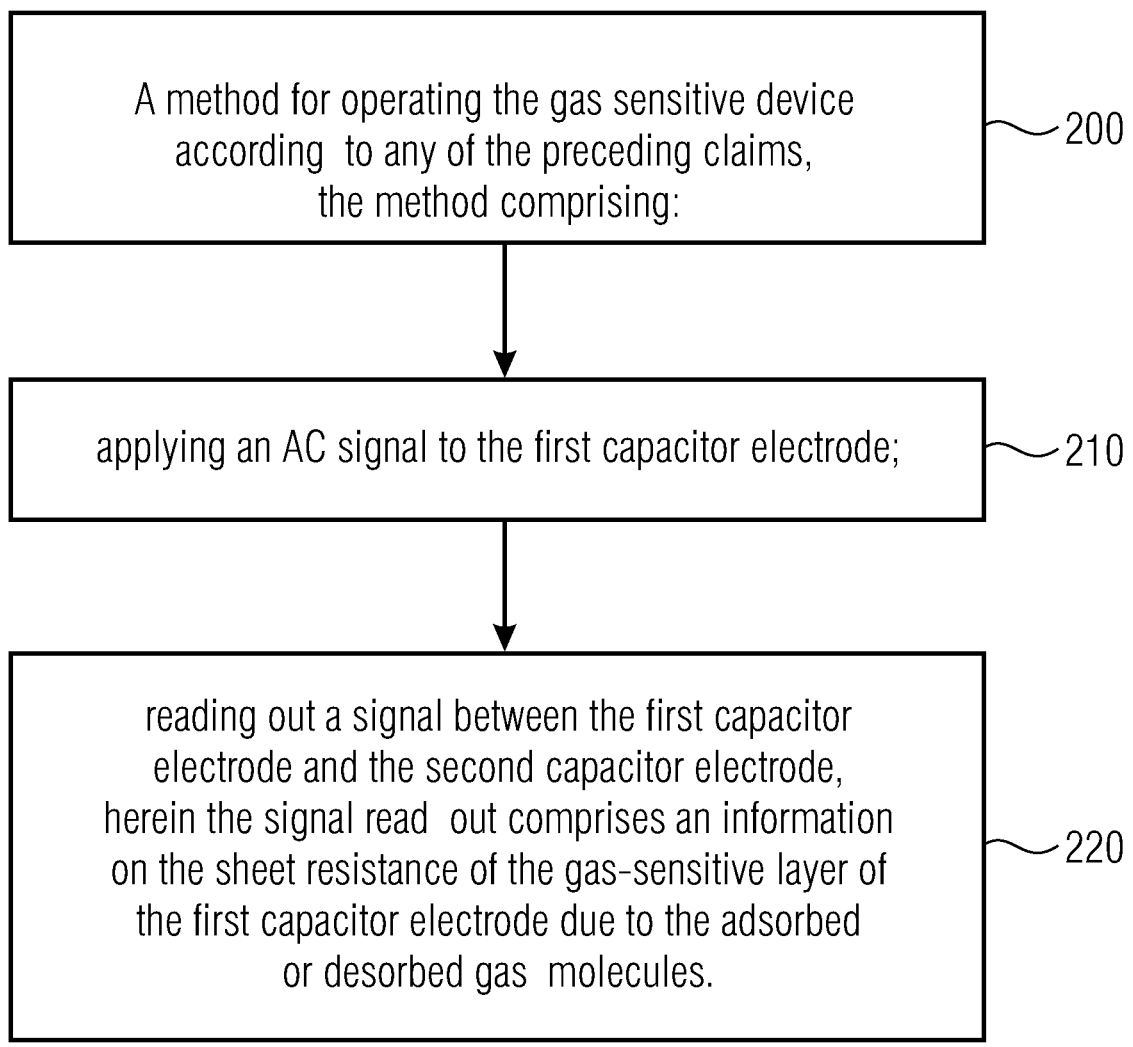
FIG. 20 shows an exemplary process flow (flowchart) of the method for operating the gas sensitive device.

According to another aspect of the present disclosure, a method for operating the gas sensitive device 10 is disclosed. FIG. 20 shows a flow chart of the principles of method for operating the gas sensitive device 10. The method 200 comprises applying an AC signal to the first capacitor electrode 40 according to a step 210 and reading out a signal between the first capacitor electrode 40 and the second capacitor electrode 60 according to step 220. The signal read out comprises information on the sheet resistance of the gas-sensitive layer 45 of the first capacitor electrode 40 due to the adsorbed or desorbed gas molecules.

Figure 8A:
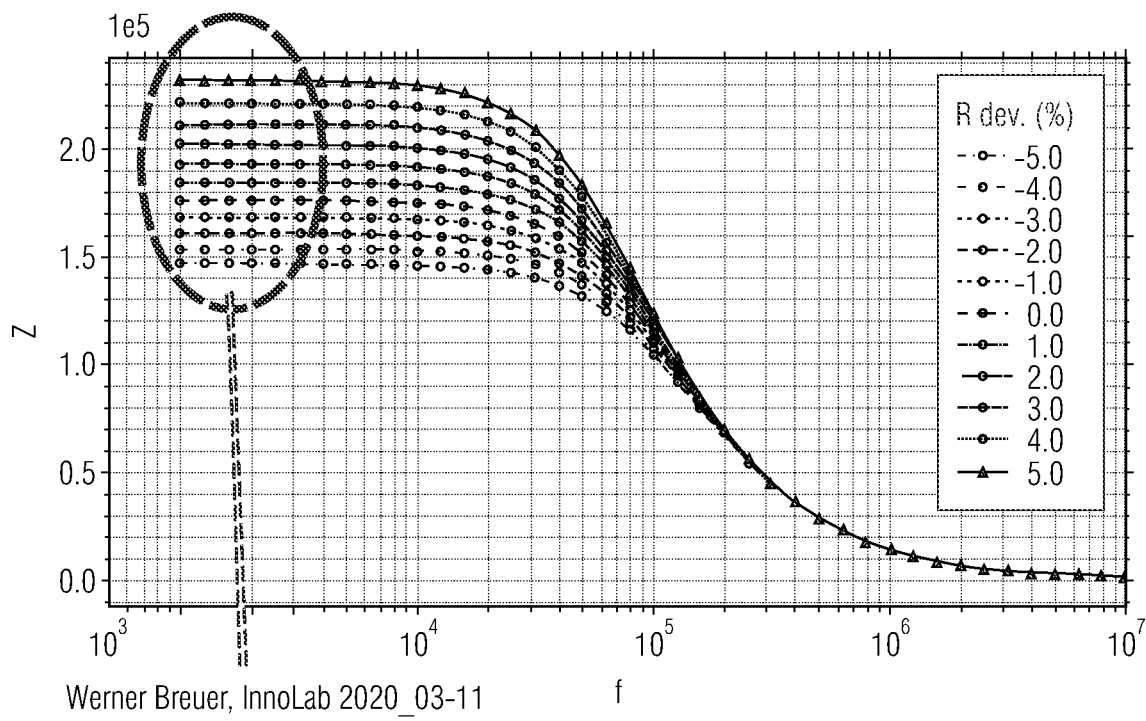
FIGS. 8a, 8b, 8c and 8d show results of different AC-measurement capabilities of the AC-coupled multi gas sensor according to an embodiment.
Figure 8B:
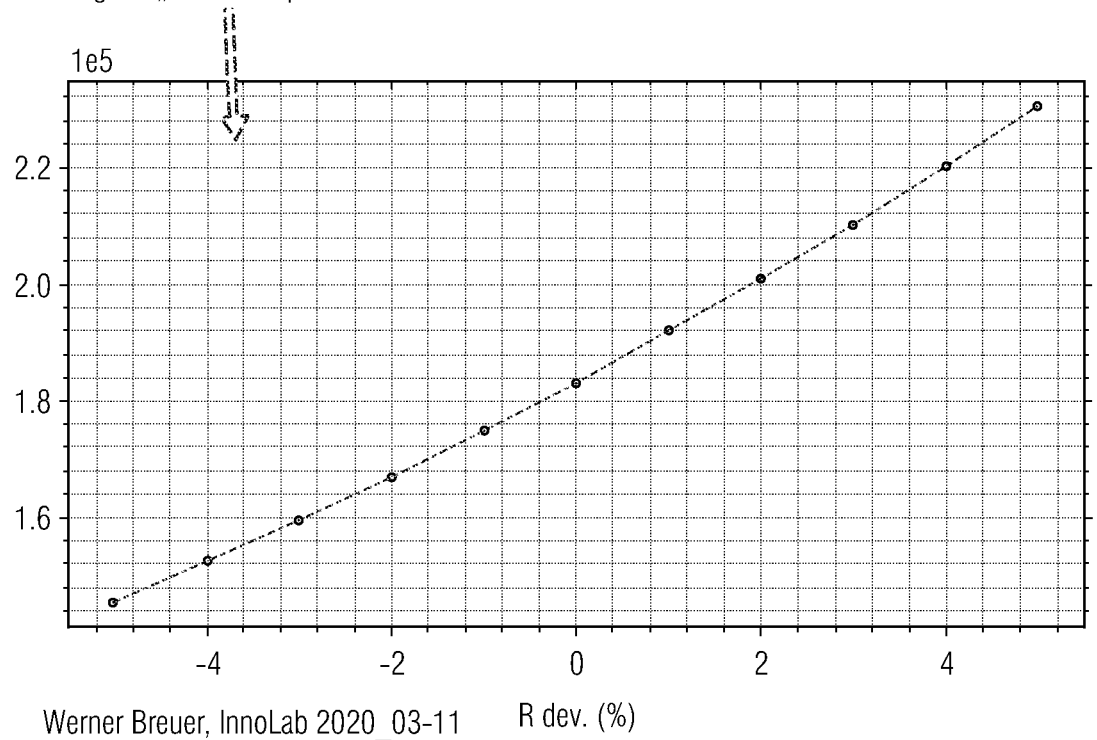
Figure 8C:
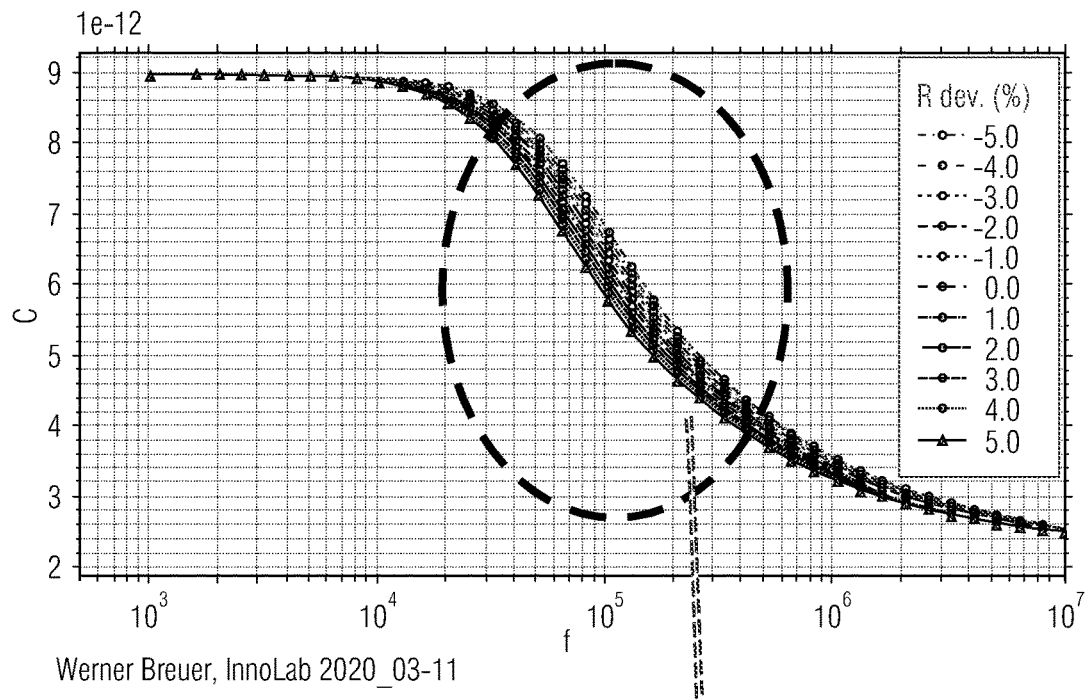
Figure 8D:
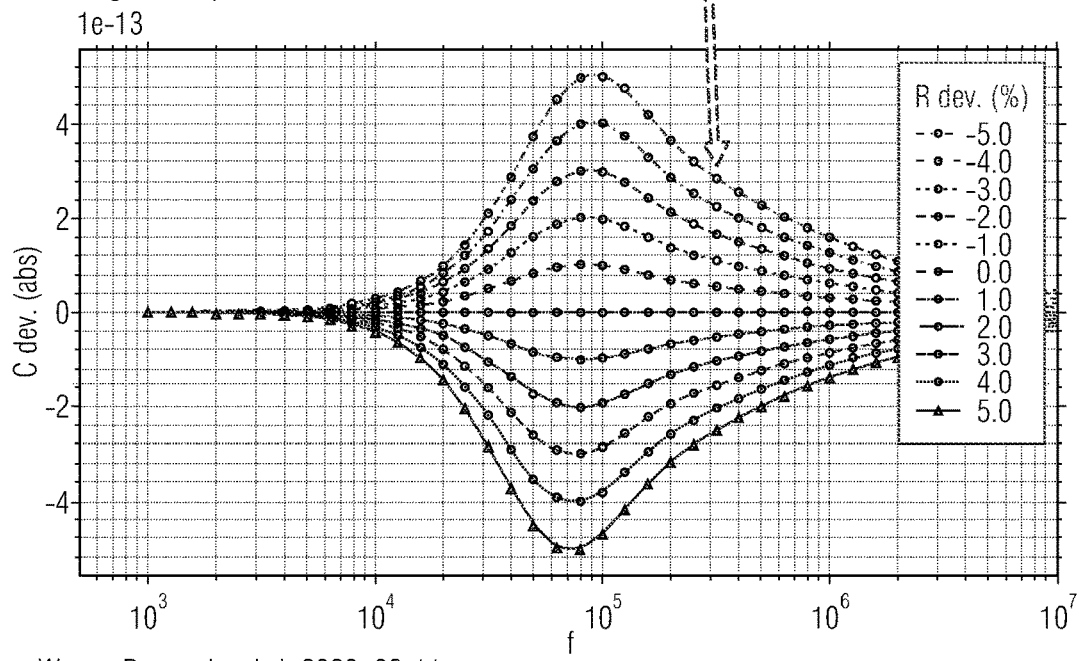

FIGS. 8a-8d show simulation results of different AC-measurement capabilities of the AC-coupled multi gas sensor when performing the proposed method 200. If measurements at low frequencies f are preformed, a change of the impedance Z will be detected. FIGS. 8a and 8b show results for measurements or simulations at low frequencies f. In FIG. 8a the impedance Z is plotted against the applied frequency f of the AC-signal. In FIG. 8b the measured or simulated impedance Z is plotted against its corresponding sheet resistance R. The sheet resistance R is the real part of the sheet impedance Z that comprises an imaginary part and a real part. At low frequencies, i.e. about f=103 Hz (see also the ellipse 81), the impedance change z and/or the resistance change R can be measured. The impedance change Z is correlated to the amount of adsorbed gas molecules. The impedance change Z may give a hint on the level of adsorbed gas molecules that are adsorbed by the gas sensitive layer 45. FIG. 8b shows the deviation of the sheet resistance in % (in percentage) form the normal value of the sheet resistance. For example, the normal values of the sheet resistance of the gas sensitive layer 45 are given by the sheet resistance in atmosphere without pollution. Without pollution means without adsorbed molecules of the pollution, for example $NO_x$, $O_3$, $CO_2$, Co or volatile organic components. The sheet resistance itself is always positive, however the deviation of the reference sheet resistance with the presence of adsorbed pollution molecules may be positive, zero or negative as can be seen in FIG. 8b. The sheet impedance at a low frequency f is correlated with the deviation of the sheet resistance R. The size of the value of the deviation of the sheet resistance may depend on the amount of adsorbed gas molecules.

In the lower figures of FIG. 8 (FIGS. 8c and 8d) the capacity C is plotted against the applied frequency f of the AC-signal. FIGS. 8c and 8d show results for measurements or simulations at high frequencies f. High frequencies f are about 105 Hz. At high or higher frequencies a detection of capacity changes will appear. For example, at frequencies between 104 Hz and 106 Hz, the capacity change C is correlated with the change of the sheet resistance R. At a sheet resistance change of ±5% at about 105 Hz the capacity change C is measured to be the highest. Where no sheet resistance change R occurs, i.e. at a sheet resistance change of 0%, no capacity change occurs.

From the results shown in FIGS. 8a to 8d it is derivable that a relation between the sheet resistance of the first electrode 40 and the capacitive impedance of the insulator layer 30 that is directly disposed between the first electrode 40 and the second electrode 60 causes a frequency dependency of the capacitance and the impedance measurements. The proposed method may further comprise applying an AC-signal to the gas sensitive capacitor; and measuring the capacitance/impedance of the whole area of the first electrode 40 at low frequencies, or measuring the capacitance at the edge of the first electrode 40 at high frequencies. By reading out the signal information about a concentration of adsorbed or desorbed molecules may be derived.

The present proposed gas sensitive device, which may be incorporated into a multi-gas sensor, provides an easy and cheap approach to determine the pollution of the ambient atmosphere with different kinds of gases, such an ozone $O_3$, carbon monoxide $C_O$, nitrogen dioxide $NO_2$ and many more different gases. The principle of the present disclosure is to provide the top electrode with a functionalized graphene layer, so that depending on the doped nanoparticles and/or doped salts different kinds of gas molecules can be detected. The top electrode thereby is provided by an ink drop with no specific topology. In this way, a gas sensitive device is provided that is independent from locally clustered graphene flakes and/or from coffee stain. Therewith, an approach to implement an improved gas sensitive device is disclosed.

Although some aspects have been described as features in the context of an apparatus it is clear that such a description may also be regarded as a description of corresponding features of a method. Although some aspects have been described as features in the context of a method, it is clear that such a description may also be regarded as a description of corresponding features concerning the functionality of an apparatus.

Additional embodiments and examples are described which may be used alone or in combination with the features and functionalities described herein.

Example embodiments of the present invention are summarized here. Other embodiments can also be understood from the entirety of the specification and the claims filed herein.

Example 1. A gas sensitive device, comprising: a substrate structure, and a gas sensitive capacitor, the gas sensitive capacitor comprising a first capacitor electrode in form of a gas-sensitive layer on a first main surface region of an insulation layer and a second capacitor electrode in form of a buried conductive region below the insulation layer, wherein the insulation layer is arranged between the first and second capacitor electrode; wherein the gas-sensitive layer comprises a sheet impedance which changes in response to the adsorption or desorption of gas molecules.

Example 2. The gas sensitive device according to example 1, wherein the gas sensitive device comprises a first contact region for electrically contacting the first capacitor electrode, and a second contact region for electrically contacting the second capacitor electrode.

Example 3. The gas sensitive device according to example 1 or 2, wherein the first contact region is ohmically coupled to the first capacitor electrode.

Example 4. The gas sensitive device according to example 3, wherein a projection of the first capacitor electrode vertically with respect to the first main surface region at least partially or completely overlaps with the second capacitor electrode.

Example 5. The gas sensitive device according to example 3 or 4, wherein the first contact region at least partially or completely surrounds and electrically contacts the first capacitor electrode.

Example 6. The gas sensitive device according to one of the examples 3 to 5, wherein the first contact region forms an area contact region or a point contact region with the first capacitor electrode or the second contact region forms an area contact region or a point contact region with the second capacitor electrode.

Example 7. The gas sensitive device according to one of the examples 2 to 6, wherein on top of the insulation layer a cover layer is disposed, so that the cover layer having at least a common plane with the first contact region and/or the first capacitor electrode surrounds the first contact region or the first contract region and the first capacitor electrode in the at least one common plane.

Example 8. The gas sensitive device according to example 7, wherein the first contact region extends from the first capacitor electrode in the at least one common plane to a position above the cover layer being in at least a plane parallel to the at least one common plane.

Example 9. The gas sensitive device according to example 2, wherein the second contact region is capacitively coupled to the second capacitor electrode, wherein the second contact region and the second capacitor electrode are arranged in the same plane of the gas sensitive device, and/or wherein the first contact region and the second capacitor electrode are arranged in different planes of the gas sensitive device.

Example 10. The gas sensitive device according to example 9, wherein the first contact region ohmically contacts a first border region of the first capacitor electrode.

Example 11. The gas sensitive device according to example 9 or 10, wherein the first contact region ohmically contacts a center region of the first capacitor electrode.

Example 12. The gas sensitive device according to one of the examples 9 to 11, wherein the second capacitor electrode capacitively contacts a second border region of the first capacitor electrode.

Example 13. The gas sensitive device according to one of the preceding examples, wherein the first main surface region of the insulation layer having the gas-sensitive layer is topology-free.

Example 14. The gas sensitive device according to one of the preceding examples, wherein the first capacitor electrode and the second capacitor electrode are arranged parallel to each other and vertical with respect to the first main surface region of the insulation layer.

Example 15. The gas sensitive device according to one of the preceding examples, wherein a third capacitor electrode is disposed apart from the second capacitor electrode, wherein the third capacitor electrode and the second capacitor electrode are positioned so that both extend along in at least one common plane.

Example 16. The gas sensitive device according to example 15, wherein the third capacitor electrode and the second capacitor electrode are spaced apart from each other in the least one common plane by a second insulation layer extending between third capacitor electrode and the second capacitor electrode.

Example 17. The gas sensitive device according to one of the preceding examples, wherein the first capacitor electrode being the gas sensitive layer is a thin and/or two-dimensional layer, the electrical conductivity of which is influenceable by an interaction with gas molecules.

Example 18. The gas sensitive device according to example 17, wherein the gas sensitive layer or the thin and/or two-dimensional layer is doped with nanoparticles and/or doped with salts for functionalizing the first electrode.

Example 19. The gas sensitive device according to one of the preceding examples, wherein the gas sensitive device comprises a heater positioned in the gas sensitive device, the heater used for bringing the gas-sensitive layer to a desired temperature or temperature profile for sensing, or for resetting the gas-sensitive layer.

Example 20. The gas sensitive device according to example 19, wherein the heater and the second capacitor electrode are separated from each other by the second insulation layer.

Example 21. The gas sensitive device according to examples 19 or 20, wherein the gas sensitive device comprises a third contact region for electrically contacting the heater.

Example 22. The gas sensitive device according to one of the examples 19 to 21, wherein the heater comprises at least on side that at least partially forms with at least a side of the substrate layer a cavity.

Example 23. The gas sensitive device according to one of the preceding examples, wherein a surrounding shape of the first electrode is different from a surrounding shape of the insulator layer or wherein a surrounding shape of the first electrode is equal to a surrounding of the insulator layer.

Example 24. The gas sensitive device according to one of the preceding examples, wherein the first electrode completely or only partially overlaps the surface of the insulator layer.

Example 25. The gas sensitive device according to one of the preceding examples, wherein a plurality of first electrodes is provided on top of the insulator layer and/or wherein a plurality of second electrodes is provided below the insulator layer, and/or wherein a plurality of first and second contact regions is provided.

Example 26. A multi-gas sensor comprising one or more gas sensitive devices according to any of the preceding examples.

Example 27. A method for operating the gas sensitive device according to any of the preceding examples, the method comprising: applying an AC signal to the first capacitor electrode; reading out a signal between the first capacitor electrode and the second capacitor electrode, wherein the signal read out comprises an information on the sheet resistance of the gas-sensitive layer of the first capacitor electrode due to the adsorbed or desorbed gas molecules.

Example 28. The method according to example 27, wherein a relation between the sheet resistance of the first electrode and the capacitive impedance of the insulator layer that is directly disposed between the first electrode and the second electrode causes a frequency dependency of a capacitance and impedance measurement so that the method comprises:
 applying an AC-signal to the gas sensitive capacitor; and
 measuring the capacitance/impedance of the whole area of the first electrode at low frequencies, or
 measuring the capacitance at the edge of the first electrode at high frequencies.

Example 29. The method according to one of the examples 27 or 28, wherein the method comprises: by reading out the signal deriving information about a concentration of adsorbed or desorbed molecules.

Depending on certain implementation requirements, embodiments of the processing device can be implemented in hardware or in software or at least partially in hardware or at least partially in software. The implementation can be performed using a digital storage medium, for example a floppy disk, a DVD, a Blu-Ray, a CD, a ROM, a PROM, an EPROM, an EEPROM or a FLASH memory, having electronically readable control signals stored thereon, which cooperate (or are capable of cooperating) with a programmable computer system such that the respective method is performed. Therefore, the digital storage medium may be computer readable. Some embodiments comprise a data carrier having electronically readable control signals, which are capable of cooperating with a programmable computer system, such that one of the methods described herein is performed.

Generally, embodiments of the processing device can be implemented as a computer program product with a program code, the program code being operative for performing one of the methods when the computer program product runs on a computer. The program code may for example be stored on a machine readable carrier. Other embodiments comprise the computer program for performing one of the methods described herein, stored on a machine readable carrier. In other words, an embodiment of the method is, therefore, a computer program having a program code for performing one of the methods described herein, when the computer program runs on a computer.

A further embodiment of the method is, therefore, a data carrier (or a digital storage medium, or a computer-readable medium) comprising, recorded thereon, the computer program for performing one of the methods described herein. The data carrier, the digital storage medium or the recorded medium are typically tangible and/or non-transitory. A further embodiment comprises a processing means, for example a computer, or a programmable logic device, configured to or adapted to perform one of the methods described herein. A further embodiment comprises a computer having installed thereon the computer program for performing one of the methods described herein.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

The apparatus described herein may be implemented using a hardware apparatus, or using a computer, or using a combination of a hardware apparatus and a computer. The methods described herein may be performed using a hardware apparatus, or using a computer, or using a combination of a hardware apparatus and a computer.

In the foregoing detailed description, it can be seen that various features are grouped together in examples for the purpose of streamlining the disclosure. This method of disclosure is not to be interpreted as reflecting an intention that the claimed examples require more features than are expressly recited in each claim. Rather, as the following claims reflect, subject matter may lie in less than all features of a single disclosed example. Thus, the following claims are hereby incorporated into the detailed description, where each claim may stand on its own as a separate example. While each claim may stand on its own as a separate example, it is to be noted that, although a dependent claim may refer in the claims to a specific combination with one or more other claims, other examples may also include a combination of the dependent claim with the subject matter of each other dependent claim or a combination of each feature with other dependent or independent claims. Such combinations are proposed herein unless it is stated that a specific combination is not intended. Furthermore, it is intended to include also features of a claim to any other independent claim even if this claim is not directly made dependent to the independent claim.

Although specific embodiments have been illustrated and described herein, it will be appreciated by those of ordinary skill in the art that a variety of alternate and/or equivalent implementations may be substituted for the specific embodiments shown and described without departing from the scope of the present embodiments. This application is intended to cover any adaptations or variations of the specific embodiments discussed herein. Therefore, it is intended that the embodiments be limited only by the claims and the equivalents thereof.

What is claimed is:

1. A gas sensitive device, comprising:
   a substrate structure; and
   a gas sensitive capacitor, the gas sensitive capacitor comprising:
      a first capacitor electrode in form of a gas sensitive layer on a first main surface region of an insulation layer,
      a second capacitor electrode in form of a buried conductive region below the insulation layer, wherein:
         the insulation layer is arranged between the first and second capacitor electrode, and
         the gas sensitive layer comprises a sheet impedance that changes in response to adsorption or desorption of gas molecules, and
      a cover layer disposed on top of the insulation layer, wherein the cover layer has at least one common plane with the first capacitor electrode, the cover layer surrounds the first capacitor electrode in the at least one common plane leaving the entire first capacitor electrode uncovered by the cover layer.

2. The gas sensitive device according to claim 1, wherein a projection of the first capacitor electrode vertically with respect to the first main surface region at least partially or completely overlaps with the second capacitor electrode.

3. The gas sensitive device according to claim 1, wherein the gas sensitive device comprises:
   a first contact region electrically contacting the first capacitor electrode; and
   a second contact region electrically contacting the second capacitor electrode.

4. The gas sensitive device according to claim 3, wherein the first contact region at least partially or completely surrounds and electrically contacts the first capacitor electrode.

5. The gas sensitive device according to claim 3, wherein the first contact region forms an area contact region or a point contact region with the first capacitor electrode or the second contact region forms an area contact region or a point contact region with the second capacitor electrode.

6. The gas sensitive device according to claim 3, wherein:
   the cover layer further has at least one common plane with the first contact region; and
   the cover layer surrounds the first contact region and the first capacitor electrode in the at least one common plane.

7. The gas sensitive device according to claim 6, wherein the first contact region extends from the first capacitor electrode in the at least one common plane to a position above the cover layer being in at least a plane parallel to the at least one common plane.

8. The gas sensitive device according to claim 3, wherein the second contact region is coupled to the second capacitor electrode, wherein
   the second contact region and the second capacitor electrode are arranged in the same plane of the gas sensitive device; or
   the second contact region and the second capacitor electrode are arranged in different planes of the gas sensitive device.

9. The gas sensitive device according to claim 8, wherein
   the first contact region contacts a first border region of the first capacitor electrode; or
   the first contact region contacts a center region of the first capacitor electrode.

10. The gas sensitive device according to claim 8, wherein the second capacitor electrode capacitively contacts a second border region of the first capacitor electrode.

11. The gas sensitive device according to claim 3, wherein at least a portion of the first contact region is disposed over the cover layer.

12. The gas sensitive device according to claim 1, wherein the first main surface region of the insulation layer having the gas sensitive layer is topology-free.

13. The gas sensitive device according to claim 1, wherein the first capacitor electrode and the second capacitor electrode are arranged parallel to each other and vertical with respect to the first main surface region of the insulation layer.

14. The gas sensitive device according to claim 1, wherein the first capacitor electrode being the gas sensitive layer is thin and/or is a two-dimensional layer, and comprises an electrical conductivity influenceable by an interaction with gas molecules.

15. The gas sensitive device according to claim 1, wherein:
   a third capacitor electrode is disposed apart from the second capacitor electrode; and
   the third capacitor electrode and the second capacitor electrode are positioned so that both the third capacitor electrode and the second capacitor electrode extend along in at least one common plane.

16. The gas sensitive device according to claim 15, wherein the third capacitor electrode and the second capacitor electrode are spaced apart from each other in the least one common plane by a second insulation layer extending between the third capacitor electrode and the second capacitor electrode.

17. The gas sensitive device according to claim 16, wherein:
the gas sensitive device comprises a heater positioned in the gas sensitive device;
the heater is configured to bring the gas sensitive layer to a desired temperature or temperature profile for sensing or for resetting the gas sensitive layer; and
the heater and the second capacitor electrode are separated from each other by the second insulation layer.

18. The gas sensitive device according to claim 17, wherein the gas sensitive device comprises a third contact region for electrically contacting the heater.

19. The gas sensitive device according to claim 17, wherein the heater comprises at least one side that at least partially forms a cavity with at least a side of the substrate structure.

20. The gas sensitive device according to claim 1, wherein:
a surrounding shape of the first capacitor electrode is different from a surrounding shape of the insulation layer; or
a surrounding shape of the first capacitor electrode is equal to the surrounding of the insulation layer; or
the first capacitor electrode completely or only partially overlaps the surface of the insulation layer.

21. The gas sensitive device according to claim 1, wherein
a plurality of first electrodes is provided on top of the insulator layer; or
a plurality of second electrodes is provided below the insulator layer, or
a plurality of first and second contact regions is provided.

22. A method of operating a gas sensitive device comprising: a substrate structure; and a gas sensitive capacitor comprising a first capacitor electrode in form of a gas sensitive layer on a first main surface region of an insulation layer, a second capacitor electrode in form of a buried conductive region below the insulation layer, and a cover layer disposed on top of the insulation layer, wherein: the insulation layer is arranged between the first and second capacitor electrode, the gas sensitive layer comprises a sheet resistance that changes in response to adsorption or desorption of gas molecules, and the cover layer has at least one common plane with the first capacitor electrode, the cover layer surrounds the first capacitor electrode in the at least one common plane leaving the entire first capacitor electrode uncovered by the cover layer, the method comprising:
applying an AC signal to the first capacitor electrode; and
reading out a signal between the first capacitor electrode and the second capacitor electrode, wherein the signal read out comprises information on the sheet resistance of the gas sensitive layer of the first capacitor electrode due to the adsorbed or desorbed gas molecules.

* * * * *